(12) United States Patent
Prien et al.

(10) Patent No.: US 11,399,811 B2
(45) Date of Patent: Aug. 2, 2022

(54) METHOD AND APPARATUS FOR COLLECTION OF FLUID SAMPLES

(71) Applicants: Texas Tech University System, Lubbock, TX (US); RSI Technology Group, LLC, Dallas, TX (US)

(72) Inventors: Samuel D. Prien, Shallowater, TX (US); Lindsay L. Penrose, Lubbock, TX (US); Diana M. Peninger, Flower Mound, TX (US)

(73) Assignees: TEXAS TECH UNIVERSITY SYSTEM, Lubbock, TX (US); RSI TECHNOLOGY GROUP, LLC, Dallas, TX (US)

( * ) Notice: Subject to any disclaimer, the term of this patent is extended or adjusted under 35 U.S.C. 154(b) by 0 days.

(21) Appl. No.: 17/364,792

(22) Filed: Jun. 30, 2021

(65) Prior Publication Data

US 2021/0401410 A1  Dec. 30, 2021

Related U.S. Application Data

(60) Provisional application No. 63/046,347, filed on Jun. 30, 2020.

(51) Int. Cl.
*A61B 10/00* (2006.01)
*B65D 1/00* (2006.01)
(Continued)

(52) U.S. Cl.
CPC ............ *A61B 10/0058* (2013.01); *B65D 1/00* (2013.01); *B65D 11/16* (2013.01); *B65D 43/02* (2013.01);
(Continued)

(58) Field of Classification Search
CPC ...... A61B 10/0058; B65D 1/00; B65D 11/16; B65D 43/02; B65D 43/0231; C08K 5/13; C08K 5/17; C08K 5/521; C08K 2201/014
See application file for complete search history.

(56) References Cited

U.S. PATENT DOCUMENTS 6,686,204 B2 * 2/2004 Dubrowny ............ B01L 3/5082
422/547
6,864,046 B1 3/2005 Prien et al.
(Continued)

FOREIGN PATENT DOCUMENTS

CA 2373907 A1 * 9/2002 ............... C08K 5/17
WO 199928379 A1 6/1999
(Continued)

OTHER PUBLICATIONS

Authorized Officer Georg Hutterer; International Search Report and Written Opinion; PCT/US2021/040017; dated Oct. 15, 2021; 23 pages.
(Continued)

*Primary Examiner* — Angela C Scott
(74) *Attorney, Agent, or Firm* — Dickinson Wright PLLC; Kristopher Lance Anderson

(57) ABSTRACT

The present invention relates in general to the improved containment of biological fluids. In particular, a method and apparatus for collection and preservation of fluid samples in accordance with the present invention results in collection of semen having improved viability both at the time of collection and after storage. The disclosed methods and apparatuses methods support a wide variety of applications for containment of biological fluids related to human and veterinary medicine including, but not limited to, human reproductive medicine and animal husbandry.

28 Claims, 4 Drawing Sheets

(51) Int. Cl.
*B65D 6/10* (2006.01)
*B65D 43/02* (2006.01)
*C08K 5/13* (2006.01)
*C08K 5/17* (2006.01)
*C08K 5/521* (2006.01)

(52) U.S. Cl.
CPC ............ *B65D 43/0231* (2013.01); *C08K 5/13* (2013.01); *C08K 5/17* (2013.01); *C08K 5/521* (2013.01); *C08K 2201/014* (2013.01)

(56) References Cited

U.S. PATENT DOCUMENTS

| | | | |
|---|---|---|---|
| 8,623,479 B2 | 1/2014 | Siegel et al. | |
| 9,968,709 B2 | 5/2018 | Muratoglu et al. | |
| 10,407,563 B2 | 9/2019 | Gupta et al. | |
| 2010/0119417 A1* | 5/2010 | Motadel | B01L 3/00 422/400 |
| 2010/0233405 A1* | 9/2010 | Andrews | C08L 67/02 524/217 |
| 2015/0265386 A1* | 9/2015 | Schmitt | A61D 19/021 604/349 |
| 2017/0325607 A1* | 11/2017 | Choltco-Devlin | A47J 41/0072 |
| 2020/0040114 A1* | 2/2020 | Hay | B29C 41/003 |
| 2021/0276007 A1* | 9/2021 | Ootani | G01N 1/12 |

FOREIGN PATENT DOCUMENTS

| | | | |
|---|---|---|---|
| WO | 200066659 A1 | 11/2000 | |
| WO | 200164936 A2 | 9/2001 | |
| WO | 2007146344 A2 | 12/2007 | |
| WO | 2010103023 A1 | 9/2010 | |
| WO | 2016009363 A1 | 1/2016 | |
| WO | WO-2020004590 A1 * | 1/2020 | ............. A61B 5/151 |

OTHER PUBLICATIONS

Wellington da Silva Oliveira, et al.; Development of an Extraction Method Using Mixture Design for the Evaluation of Migration of Non-Target Compounds and Dibutyl Phthalate from Baby Bottles; Food Anal. Methods (2017)10, pp. 2619-2328; Jan. 31, 2017.
https://web.archive org/web/20180901115127/https://reproductive.solutions/How ProteX can help, 1 page.
Jen-Taut Yeh, et al.; White Spirit Permeation Resistance of Polyethylene, Polyethylene/Modified Polyamide, and Polyethylene/Blends of Modified Polyamide and Ethylene Vinyl Alcohol Bottles; Polymer Engineering and Science, 2005; pp. 25-32.

* cited by examiner

METHOD AND APPARATUS FOR COLLECTION OF FLUID SAMPLES

CROSS-REFERENCE TO RELATED APPLICATIONS

This application claims priority of U.S. Provisional Patent Application Ser. No. 63/046,347, entitled "IMPROVED SEMEN COLLECTION DEVICE," filed on Jun. 30, 2020, the contents of which are incorporated by reference herein in their entirety.

FIELD OF THE INVENTION

The present invention relates in general to the containment of biological fluids and, in specific embodiments, to collection of samples of biological fluids in relation to the field of assisted reproductive technologies. In particular, a method and apparatus for collection and preservation of fluid samples in accordance with the present invention results in collection of semen samples having improved viability both at the time of collection and after storage. The disclosed methods and apparatuses support a wide variety of applications for containment of or contact with biological fluids related to human and veterinary medicine and medical devices including, but not limited to, human reproductive medicine and animal husbandry.

BACKGROUND OF THE INVENTION

Assisted reproductive technologies were developed originally to treat individuals with obstructed ovarian tubes, but have matured to procedures which, according to the U.S. Center for Disease Control (2013), now accounts for up to 2% of the annual U.S. birth rate. Since the first human birth from in vitro fertilization in 1978, there have been significant improvements in stimulation protocols, fertilization and culture techniques, use of donor gametes and embryos, and patient selection. Further, the use of pre-implantation genetic diagnosis/pre-implantation genetic screening, an invasive harvesting of cells for genetic screening, has allowed improved selection of embryos to avoid aneuploidy and other genetic defects. These improvements resulted in constantly increasing pregnancy rates while allowing a steady decrease in the number of embryos transferred (Center for Disease Control, 25 2013).

U.S. Pat. No. 6,864,046, incorporated by reference herein in its entirety, discloses the use of a method for collecting the semen of an animal via a semen collection vessel having a semen extender solution capable of extending motility of collected semen. Such semen collection vessel is capable of extending the life of spermatozoa, and further improves conditions when utilized in connection with a semen extender solution, which may contain several ingredients including, but not limited to, nutrients to maintain its metabolic activity and to undergo the processes necessary for fertilization of the ova, proteins necessary for the sperm cells to grow and to mature into the spermatozoa, sugars to provide the sperm with energy, antimicrobial agents to reduce microbial contamination and prevent the spread of diseases that can be transported in the semen, and cryoprotectants to protect spermatozoa from damage due to ice crystal formation when frozen. This well-developed field has long-utilized semen extenders for improving the life of the collected samples. However, with the increase of cryopreservation, as well as the advancing state of the art in reproductive sciences, there remains a need for further enhancing the collection and storage of semen for improved semen quality and protection.

In addition to these traditional motivations, the recent pandemic has resulted in behavioral changes promoting a need for improved preservation of semen samples. It has been found that a shift for collection at clinic to at home for the population examined resulted in an increase in the time from collection to completed preparation. This has been shown to significantly effect the viability of useful sperm samples.

Therefore, there is a need for collection and/or storage containers, medical devices, and related processes that improve the viability of sperm, in collected semen and/or extend the time period for which such sperm remains viable.

SUMMARY OF THE INVENTION

In general, the present disclosure relates to apparatuses and methods for collection, processing, and/or storage of biological fluids susceptible to degradation by oxidation. In particular, apparatuses and methods for collection and/or storage of mammalian semen samples are disclosed herein. The invention is further directed to apparatus, collections device and other medical devices that control free oxygen radicals within a biological fluid, and where this biological fluid is sperm, the amount of time available before a sperm must be used to fertilize an egg is increased.

In some embodiments, an apparatus for collection of fluids comprises a first vessel. The first vessel includes an upper portion and a lower portion. The upper portion is a wall, which can be of any suitable profile. The lower portion is a reservoir having a volume and capacity. The wall and reservoir are joined such that the inner surface of the reservoir and the inner surface of the wall form a continuous surface. A suitable profile for the wall is one that will be effective as a collection means to cause liquid entering the top of the first vessel to collect in the reservoir by gravity flow. A portion or all of the inner surface of the reservoir, a portion or all of the inner surface of the wall, or a portion or all of the combined inner surface of the wall and reservoir, comprise an antioxidant in an amount effective to reduce oxidation damage to collected biological fluid, specifically semen samples. The apparatus can further include a lid suitable as sealable attachment to the first vessel. The inner surface of the lid can also comprise an antioxidant.

In some embodiments, an apparatus for collection of fluids comprises a first vessel and a second vessel. In these embodiments, the first vessel is as described above, but additionally the first and second vessels are of sizes and shapes to permit the first vessel to be inserted into the second vessel. When so inserted, the upper edges of the first and second vessels are proximate to one another and are substantially congruent. In some embodiments, the upper edges of the first and second vessels are connected or secured to one other by a threaded connection, a snap connection, or other common means.

In some embodiments, the first vessel comprises a reservoir and optionally a reservoir seal means.

In some embodiments, the medical device for collecting, storing, and/or processing biological fluids has at least one component having a surface to which the biological fluid contact, wherein the surface comprises an antioxidant in an amount sufficient to reduce oxidation degradation of the biological fluid.

In some embodiments, in addition to any or all of the above attributes, the first vessel, second vessel, reservoir seal means, and/or lid can comprise a polymer, preferably a thermoplastic. In some embodiments, any polymer that can be molded can be used for fabrication of the first vessel, second vessel, reservoir seal means, and/or lid.

In some embodiments, in addition to any or all of the above attributes, a polymer, composition, preferably a thermoplastic, or in some cases a thermoset, composition, is provided wherein the composition has a surface comprising an antioxidant in an amount effective to reduce or slow oxidative degradation of a fluid in contact with the surface. In some embodiments, the amount of any one or more antioxidant in the polymer or thermoplastic composition is less than 0.1 weight percent based on the total weight of the composition.

In some embodiments, a method for collecting and/or storing semen comprises contacting semen with a surface comprising a thermoplastic composition having one or more antioxidant.

In some embodiments, an apparatus for collecting and/or storing semen is manufactured from a thermoplastic composition containing an antioxidant under heat sufficient to form a thermoplastic melt suitable for injection molding, blow molding, or roto-molding, respectively. In some embodiments, an apparatus for collecting and/or storing semen is manufactured by bonding a layer of a thermoplastic composition comprising an antioxidant to the inner surface of a vessel.

In another embodiment, a polymer and an antioxidant are made into a film, where the film is applied to the inner surface of a vessel for collecting and/or storing a biological or bodily fluid. The film can be applied by any method including thermal lamination or application of adhesive or by dissolving a polymer in a solvent along with an antioxidant, applying the solvent to the target surface and evaporating the solvent to leave an adhered polymer film layer. In some embodiments, in addition to the above attributes, the first antioxidant is chemically and/or physically bonded to the first inner surface in any manner effective to produce active antioxidant species on the surface. Methods to accomplish this include but are not limited to blending an antioxidant into a polymer from which the vessel is formed, laminating a antioxidant-containing film to the surface (either thermally or by adhesive), by extrusion of an antioxidant-containing polymer onto the surface, or by dissolving a polymer in a solvent along with an antioxidant, applying the solvent to the target surface and evaporating the solvent to leave an adhered polymer film layer.

In the embodiments above, the apparatus is manufactured from one or more polymer compositions that comprise one or more antioxidants from the group consisting of: phenolics, aromatic amines, sterically hindered amines, hydroxylamines, phosphites and phosphonites. In one preferred embodiment, the antioxidants are one or more of aromatic amines and sterically hindered amines, most preferably sterically hindered amines. In yet another embodiment, where the antioxidant is a phenolic it is preferable that the phenolic antioxidant has one or more of: a molecular weight greater than or equal to 600, 700, or 800 grams/mole; a melting temperature greater than or equal to 60° C., 70° C., or 80° C.; and a linear molecular structure substantially free of sidechains. In yet another embodiment, the amount of any one of the above antioxidants based on the total weight of the polymer and antioxidant is less than 0.1 weight percent, preferably less than 0.05 weight percent. In still yet another embodiment the total weight percent of all antioxidants within the polymer composition (including antioxidant) of the invention is less than 0.25 weight percent, preferably less than 0.2 weight percent, more preferably less than 0.15 weight percent and most preferably less than 0.1 weight percent, based on the total weight of the polymer composition (including antioxidant).

The foregoing has outlined rather broadly the features and technical advantages of the present invention in order that the detailed description of the invention that follows may be better understood. Additional features and advantages of the invention will be described hereinafter, which form the subject matter of the claims of the invention. It should be appreciated by those skilled in the art that the conception and specific embodiments disclosed may be readily utilized as a basis for modifying or designing other film structures and/or processes for carrying out the same purposes of the present invention. It should also be realized by those skilled in the art that such equivalent constructions do not depart from the spirit and scope of the invention as set forth in the appended claims. The novel features which are believed to be characteristic of the invention, both as to its structure and method of manufacture, together with further objects and advantages will be better understood from the following description.

BRIEF DESCRIPTION OF THE DRAWINGS

The present disclosure is illustrated by way of example, and not by way of limitation, in the accompanying drawings, in which like reference characters refer to like parts throughout, and in which.

DETAILED DESCRIPTION OF THE INVENTION

Figure 1:
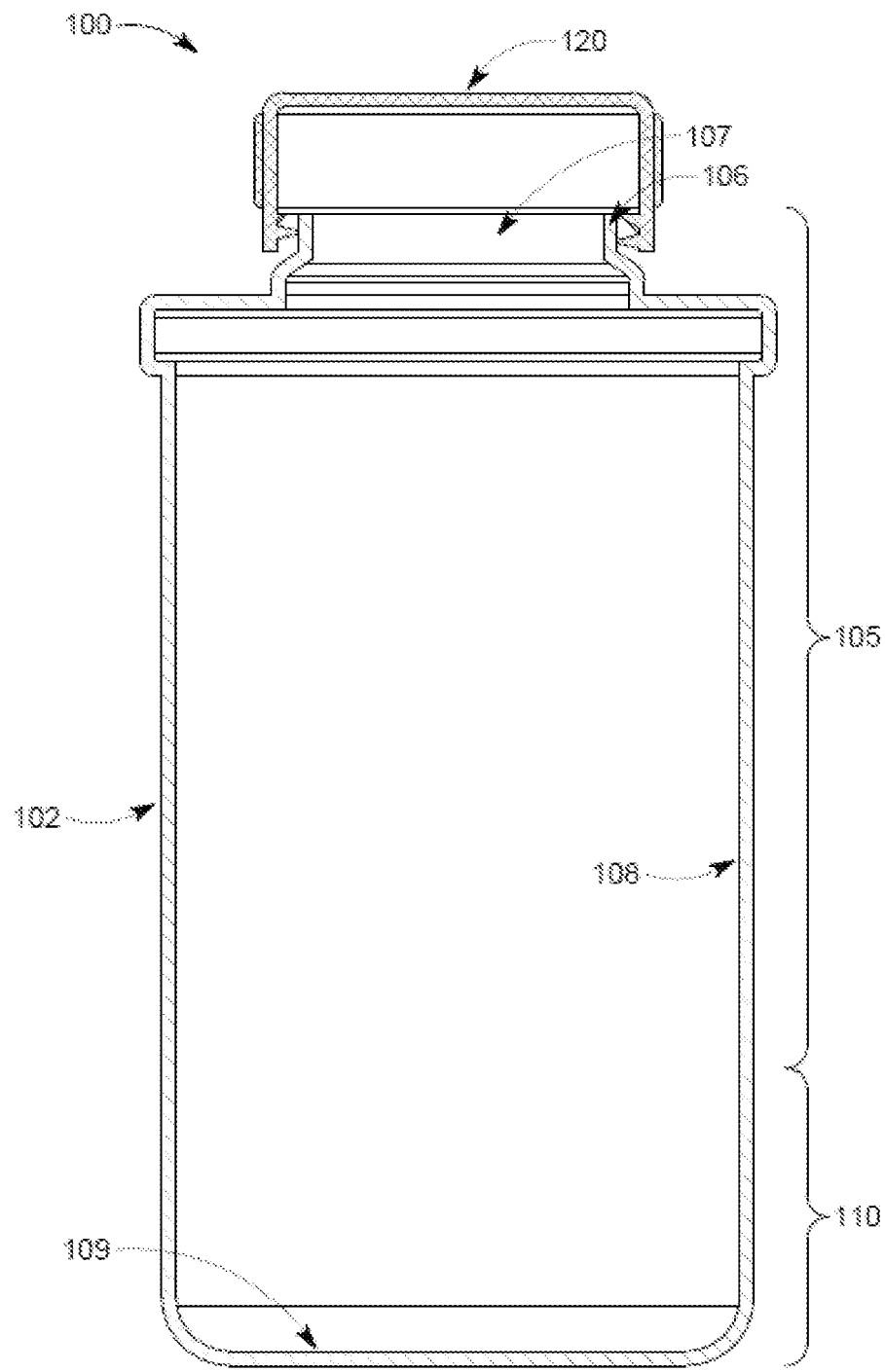
FIG. 1 shows a vertical cross-section of an embodiment employing a first vessel.

Illustrative embodiments of the subject matter claimed below will now be disclosed. In the interest of clarity, some features of some actual implementations may not be described in this specification. It will be appreciated that in the development of any such actual embodiments, numerous implementation-specific decisions must be made to achieve the developer's specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than the broadest meaning understood by skilled artisans, such a special or clarifying definition will be expressly set forth in the specification in a definitional manner that provides the special or clarifying definition for the term or phrase. It must also be noted that, as used in the specification and the appended claims, the singular forms "a," "an," and "the" include plural references unless otherwise specified.

For example, the following discussion contains a non-exhaustive list of definitions of several specific terms used in this disclosure (other terms may be defined or clarified in a definitional manner elsewhere herein). These definitions are intended to clarify the meanings of the terms used herein. It is believed that the terms are used in a manner consistent with their ordinary meaning, but the definitions are nonetheless specified here for clarity.

Definitions

"Blow molding," as used herein, means a manufacturing process that allows hollow plastic parts to be formed. Air pressure is used to inflate soft plastic into a mold cavity. The three main types of blow molding are: extrusion blow molding, injection blow molding, and injection stretch blow molding.

"Injection molding," as used herein, means a manufacturing process where material is fed into a heated barrel where it is also melted. When smooth enough, the material is injected through a nozzle under pressure (filling cycle) to fill a mold cavity and then cools off (cooling cycle). Thereafter, the mold opens and the part ejects.

"Lower end," as used herein, with respect to the apparatus or component of the apparatus means the portion of apparatus or component of the apparatus, respectively, proximate to the bottom of the apparatus or component of the apparatus, respectively, when the apparatus is in the upright orientation resting on a horizontal surface. FIG. 1, FIG. 2, FIG. 3, and FIG. 4 each show embodiments of the apparatus in the upright orientation.

"Mate," as used herein, with respect to the apparatus means to form a connection between two components of the apparatus, such as between a lid and an edge or between two edges. Examples of such connections include, but are not limited to, overlapping edges, threaded connections, and tongue and groove connections. Connections can be self-securing, such as threaded connections or overlapping edges with interference such that the edges snap together. Alternatively, connections can be such that the components fit together but require external means such as tape to secure the connection.

"Thermoplastic," as used herein, means any polymer including but not limited to acrylonitrile butadiene styrene ("ABS"), polyamide ("PA"), polybutylene terephthalate ("PBT"), polycaprolactam, polycarbonate ("PC"), polyether ether ketone ("PEEK"), polyetherimide, polyethylene ("PE"), polyethylene terephthalate ("PETE"), polymethyl methacrylate ("PMMA"), polyoxymethylene ("POM"), polyphenylene sulfide ("PPS"), polyphenylsulfone, polypropylene ("PP"), polystyrene ("PS"), polyvinylidene fluoride ("PVDF"), styrene acrylonitrile resin ("SAN"), thermoplastic elastomers ("TPE"), thermoplastic polyurethane ("TPU"), or combinations thereof.

Figure 2:
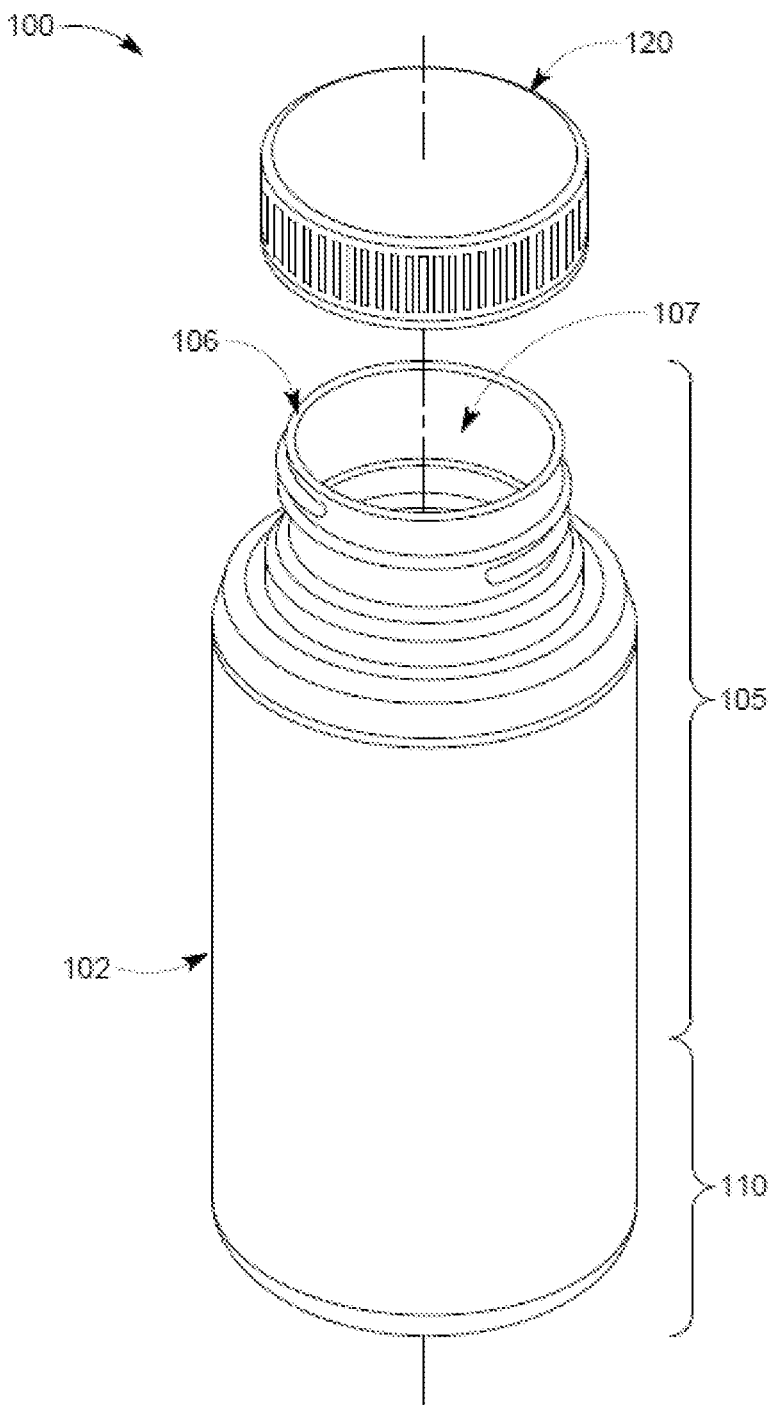
FIG. 2 shows an expanded view of the components of an embodiment employing a first vessel.

"Upper end," as used herein, with respect to the apparatus or component of the apparatus means the portion of apparatus or component of the apparatus, respectively, proximate to the bottom of the apparatus or component of the apparatus, respectively, when the apparatus is in the upright orientation resting on a horizontal surface. FIG. 1 and FIG. 2 show embodiments of the apparatus in the upright orientation.

Physical Configuration of Apparatus
Single-Vessel Embodiments

In some embodiments, as shown in FIG. 1 and FIG. 2, the apparatus 100 comprises a single vessel. FIG. 1 and FIG. 2 show different views of the same apparatus 100 and accordingly use common reference numbers for components and portions of the apparatus 100. FIG. 1 shows a vertical cross-section view of the apparatus 100 comprising vessel 102 and related components. FIG. 2 shows a corresponding three-dimensional expanded view of apparatus 100 comprising vessel 102 and its related components. The vessel 102 comprises at its upper end collection means 105 and at its lower end a reservoir 110. The single vessel 102 in these embodiments is referred to elsewhere in this disclosure and in the claims as a first vessel.

The collection means 105 as shown if FIG. 1 is essentially a vertical wall, which is cylindrical in shape. However, the wall of the collection means 105, when viewed as a vertical cross-section of the vessel can be straight, curved, sloped, or any combination thereof. When liquid is added to the vessel from above, the shape of the wall of the collection means 105 will either guide the flow of liquid by gravity or alternatively not restrict the flow by gravity of liquid toward the reservoir 110.

When viewed as a horizontal cross-section, the wall of the collection means can be circular, oval-shaped, substantially square, substantially rectangular, irregularly shaped, or any other shape as can conveniently meet user preferences for ease of manufacturing, handling, and or storage of the apparatus. The horizontal cross-section can also be variable provided that the wall of the collection means guides fluids entering the top of the vessel by gravity flow toward the reservoir or does not restrict flow of fluids entering the top of the vessel toward the reservoir.

The collection means 105 has, at its upper end, an edge 106 which defines an opening 107. Biological or bodily fluid is added to the apparatus through the opening 107 when the apparatus is used for collecting and storing the fluid, such as mammalian semen. The edge 106 and opening 107 shown in FIG. 1 are circular in shape. However, the edge 106 and opening 107 can be of any shape or size to accommodate convenient collection of semen samples from humans or from various mammalian animals.

In some embodiments, in addition to the above aspects of the physical configuration of the apparatus, the inner surface 108 of the wall of the collection means is configured to have an increased ratio of surface area of the inner surface 108 of the collection means to the volume of the collection means 105. Means for increasing this ratio include, but are not limited to, one or more nubs, one or more circumferential ridges, one or more radial fins, or combinations thereof. Increasing the surface area increases the volume of fluid in direct contact with the surface on the apparatus.

The reservoir 110 has a volume suited for the amount of fluid to be collected in the apparatus. The volume for collection of semen is based on the amount of ejaculate from the species from which the semen will be collected, whether human or other mammalian animal.

In some embodiments, in addition to the above aspects of the physical configuration of the apparatus, the inner surface 109 of the reservoir is configured to have an increased ratio of surface area of the inner surface 109 of the reservoir to the volume of the reservoir 110. Means for increasing this ratio are discussed above.

In some embodiments, in addition to the above aspects of the physical configuration of the apparatus, a closure means or lid 120 is provided to eliminate the possibility of spillage.

The lid 120 shown in FIG. 1 is circular in shape. However, the lid 120 can be of any shape or size, provided that it is configured to mate with the edge 106 at the upper end of the collection means 105, and to completely cover the opening 107.

In some embodiments, in addition to the above aspects of the physical configuration of the apparatus, the components of the apparatus are manufactured from one or more polymer compositions that contain one or more antioxidants selected from one or more of group consisting of: phenolics, aromatic amines, sterically hindered amines, hydroxylamines, phosphites, and phosphonites. In one preferred embodiment, polymer compositions comprises a polymer and an antioxidant, where the preferred antioxidant is one or more of aromatic amines and sterically hindered amines, most preferably sterically hindered amines In yet another embodiment, where the antioxidant is phenolic, it is preferable that the phenolic antioxidant has one or more of: a molecular weight greater than or equal to 600, 700, or 800 grams/mole; and a melting temperature greater than or equal to 60° C., 70° C., or 80° C.; and a linear molecular structure substantially free of sidechains.

Two-Vessel Embodiments

Figure 3:
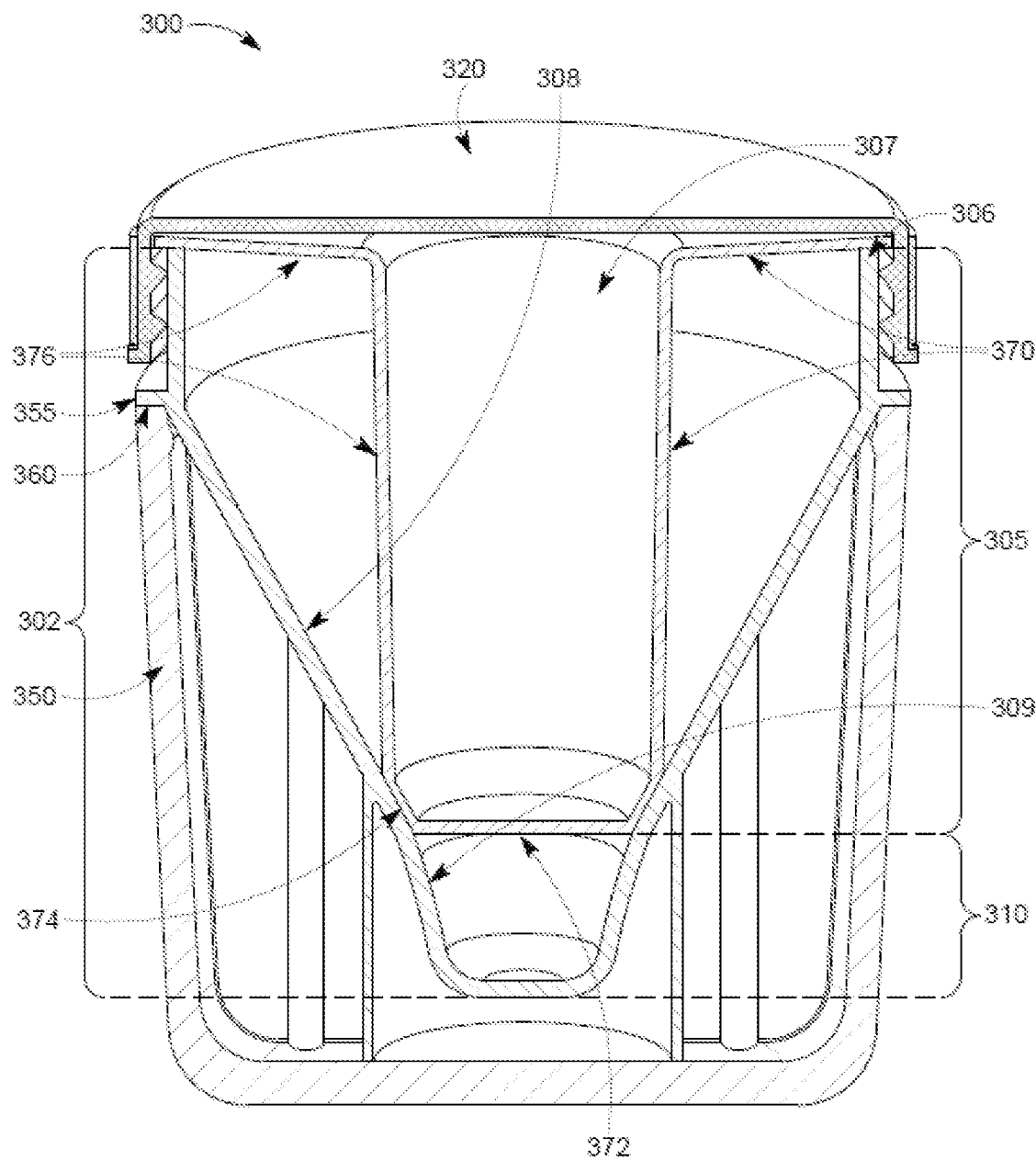
FIG. 3 shows a vertical cross-section of an embodiment employing a first and a second vessel.
Figure 4:
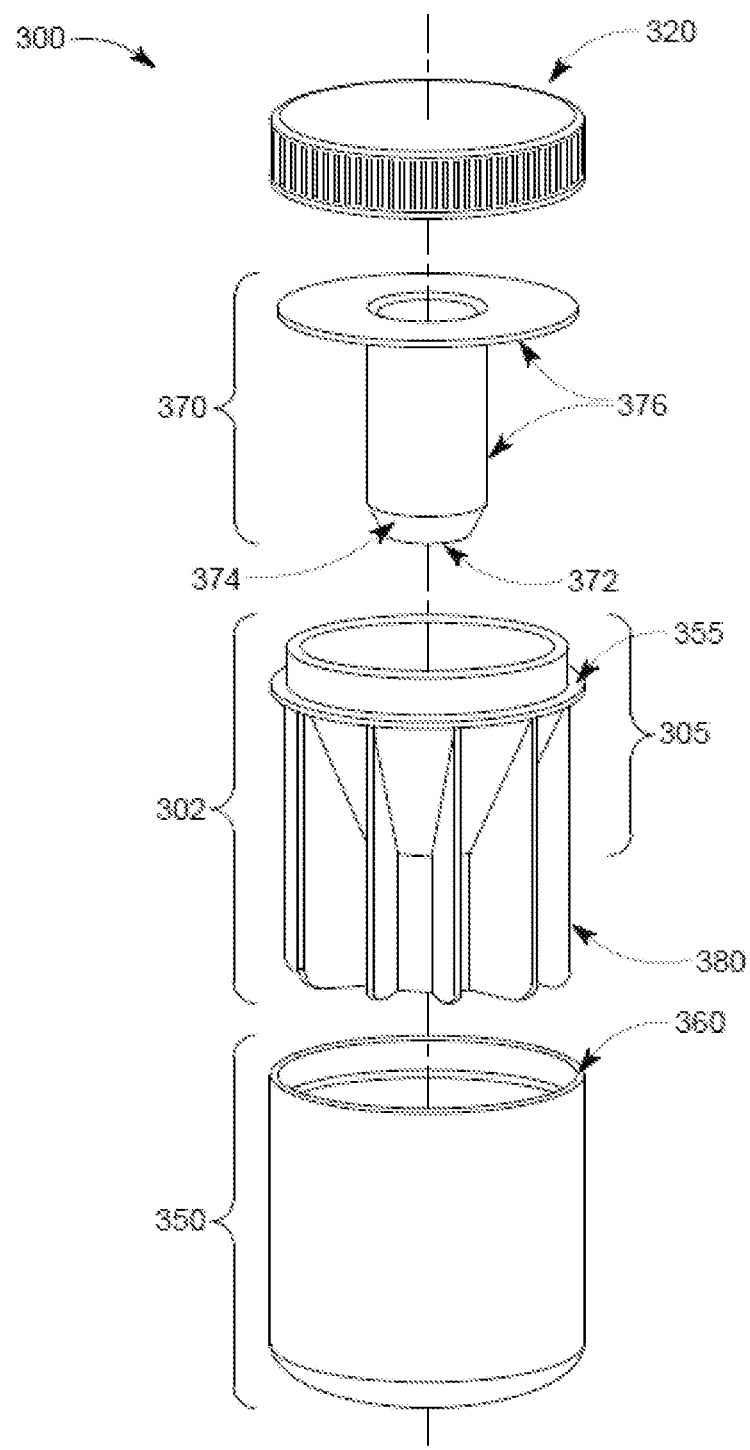
FIG. 4 shows an expanded view of the components of an embodiment employing a first vessel and a second vessel.

In some embodiments, as shown in FIG. 3 and FIG. 4, the apparatus 300 comprises a single vessel. FIG. 3 and FIG. 4 show different views of the same apparatus 300 and accordingly use common reference numbers for components and portions of the apparatus 300. FIG. 3 shows a vertical cross-section view of the apparatus 300 comprising vessel 302 and related components. FIG. 4 shows a corresponding three-dimensional expanded view of apparatus 300 comprising vessel 302 and its related components. The vessel 302 comprises at its upper end collection means 305 and at its lower end a reservoir 310. The vessel 302 in these embodiments is referred to elsewhere in this disclosure and in the claims as a first vessel.

Vessel 302 and vessel 350 are sized and shaped to allow vessel 302 to be inserted into vessel 350. When so inserted, a support 355 proximate to the upper end of the collection means 305 is suited to mate with upper edge 360 of vessel 350. The support 355 is suited to support vessel 302 substantially upright when vessel 302 is inserted into vessel 350 and when support 355 is resting on or mated with edge 360 of vessel 350. In some embodiments, support 355 and edge 360 are connected or secured to one other by a threaded connection, a snap connection, or other convenient means. Additional support members 380, including but not limited to fins as shown in FIG. 4, can also be added to the outside of vessel 302 to provide additional support to maintain vessel 302 upright whether inserted in vessel 350 or placed on a flat surface. Support members can optionally be attached to vessel 350 or not attached to either vessel. In some embodiments, the inner surface of vessel 350 and the outer surface of vessel 302 form a chamber. In some embodiments, insulation means is installed in the chamber.

The vessel 350 in these embodiments is referred to elsewhere in this disclosure and in the claims as a second vessel.

The collection means 305 as shown if FIG. 3 and FIG. 4 is essentially a sloped wall, which is conical in shape. However, the wall of the collection means 305, when viewed as a vertical cross-section of the vessel can be straight, curved, sloped, or any combination thereof. When liquid, a bodily fluid, is added to the vessel from above, the shape of the wall of the collection means 305 will either guide the flow of liquid by gravity or alternatively not restrict the flow by gravity of liquid toward the reservoir 310.

When viewed as a horizontal cross-section, the wall of the collection means 305 can be circular, oval-shaped, substantially square, substantially rectangular, irregularly shaped, or any other shape as can conveniently meet user preferences for ease of manufacturing, handling, and or storage of the apparatus. The horizontal cross-section can also be variable provided that the wall of the collection means 305 guides fluids entering the top of the vessel by gravity flow toward the reservoir 310 or does not restrict flow of fluids entering the top of the vessel toward the reservoir 310.

The collection means 305 has, at its upper end, an edge 306 which defines an opening 307. Fluid is added to the apparatus through the opening 307 when the apparatus is used for collecting and storing fluid samples, such as mammalian semen. The edge 306 and opening 307 shown in FIG. 3 and FIG. 4 are circular in shape. However, the edge 306 and opening 307 can be of any shape or size to accommodate convenient collection of semen samples from humans or from various mammalian animals.

In some embodiments, in addition to the above aspects of the physical configuration of the apparatus, the inner surface 308 of the wall of the collection means is configured to have an increased ratio of surface area of the inner surface 308 of the collection means to the volume of the collection means 310. Geometric surface features can be used as a means for increasing this ratio include, but are not limited to, one or more nubs, one or more circumferential ridges, one or more radial fins, or combinations thereof.

The reservoir 310 has a volume suited for the amount of fluid to be collected in the apparatus. The volume for collection of semen is based on the amount of ejaculate from the species from which the semen sample will be collected, whether human or other mammalian animal.

In some embodiments, in addition to the above aspects of the physical configuration of the apparatus, the inner surface 309 of the reservoir is configured to have an increased ratio of surface area of the inner surface 309 of the reservoir to the volume of the reservoir 310. Geometric surface features can be used as a means for increasing this ratio include, but are not limited to, one or more nubs, one or more circumferential ridges, one or more radial fins, or combinations thereof. Geometric surface features alternatively or further comprise surface area from a separate portion of polymer (containing antioxidant as described elsewhere herein) such as, but not limited to, adding one or more polymer pellets or beads to the space in the reservoir occupied or to be occupied by a fluid sample, wherein the surface of the beads comprise antioxidant.

In some embodiments, in addition to the above aspects of the physical configuration of the apparatus, a closure means or lid 320 is provided. The lid 320 shown in FIG. 3 and FIG. 4 is circular in shape. However, the lid 320 can be of any shape or size, provided that it is configured to mate with the edge 306 at the upper end of the collection means 305 and to completely cover the opening 307.

In some embodiments, in addition to the above aspects of the physical configuration of the apparatus, the apparatus further includes a reservoir seal means 370. The reservoir seal means 370 has at its lower end a bottom surface 372 surrounded by a seating surface 374 and at its upper end a means for providing sealing force 376. When the reservoir sealing means 370 is installed between the first vessel 300 and the lid 320, the means for providing sealing force 376 causes the seating surface to engage the first vessel proximate the junction between the reservoir 310 and the collection means 305 such that the inner surface 309 of the reservoir and the bottom surface 372 define an enclosed chamber. When the lid 320 is fully installed, the means for providing sealing force 376 both provides force to create and maintain a seal between the seating surface 374 and the first vessel 300 and thereby retain a fluid sample in the enclosed chamber defined by the bottom surface 372 of the reservoir seal means 370 and the inner surface 309 of the reservoir regardless of the spatial orientation of the apparatus 300. The reservoir seal means 370 shown in FIG. 3 and FIG. 4 has a cylindrical body with a bottom surface 372 surrounded by a seating surface 374 at its lower end and a flexible flange at its upper end as a means for providing sealing force 376. Full closure of the lid 320 causes the flange to flex to provide the seal between the seating surface 374 and the first vessel 300. The means for providing sealing force 376 can also be provided without the flexible flange by selecting a length for the body of the means for providing sealing force 376 that causes an interference fit of the means for providing sealing force 376 between the lid 320, when fully engaged, and the first vessel 300, such sealing force being produced by flexure of the lid 300 and/or compression of the means for providing sealing force 376. The body of the means for providing sealing force 376 is not restricted to the two configurations described above and can be any configuration such as, but not limited to, one or more columns, a slotted hollow cylinder, a cylinder with vertical corrugations, a cylinder with horizontal corrugations, a flexible bellows, a cylindrical member of variable horizontal cross-section, or any other configuration provided that a seal between the seating surface 374 and the first vessel 300 is induced by engagement of the lid 320 to the first vessel 300. In other embodiments, the reservoir seal means can be independent of interaction with the lid, such as, but not limited to a plug or stopper engaging the seating surface 374 by interference fit.

In some embodiments, in addition to the above aspects of the physical configuration of the apparatus or medical device, the components of which are manufactured from a polymer composition comprising one or more polymers and one or more antioxidants from phenolics, aromatic amines, sterically hindered amines, hydroxylamines, phosphites, and phosphonites. In one preferred embodiment, the antioxidants are one or more of aromatic amines and sterically hindered amines, most preferably sterically hindered amines. In yet another embodiment, where the antioxidant is a phenolic it is preferable that the phenolic antioxidant has one or more of: a molecular weight greater than or equal to 600, 700, or 800 grams/mole; a melting temperature greater than or equal to 60° C., 70° C., or 80° C.; and a linear molecular structure substantially free of sidechains.

Functional Aspects of the Apparatus

In some embodiments, at least a portion of the inner surface 109 or 309 of the reservoir 110 or 310, respectively, contains an antioxidant. In some embodiments, substantially all or all of the inner surface 109 or 309 of the reservoir 110 or 310, respectively, contains an antioxidant.

In some embodiments, the antioxidant on the inner surface 109 or 309 of the reservoir 110 or 310 made from a polymer composition, respectively, where the polymer composition comprises a polymer and one or more of: a) a phenolic antioxidant having a melting point greater than or equal to 60° C.; b) an aromatic amine; c) a sterically hindered amine; d) a hydroxylamine; e) an amine oxide derivative; and f) less than or equal to 0.1 wt. %, 0.08 wt. %, 0.05 wt. %, or 0.02 wt. % phosphite and/or phosphonite based on the weight of the polymer and the antioxidant.

In some embodiments, the antioxidant on the inner surface 109 or 309 of the reservoir 110 or 310, respectively, is produced by blending an antioxidant with a polymer from which vessel 100 or 302 is manufactured, wherein the antioxidant comprises one or more of: a) a phenolic antioxidant having a melting point greater than or equal to 60° C.; b) an aromatic amine; c) a sterically hindered amine; d) a hydroxylamine; and e) an amine oxide derivative.

In some embodiments, the antioxidant on the inner surface 109 or 309 of the reservoir 110 or 310, respectively, is produced by blending an antioxidant with a polymer from which vessel 100 or 302 is manufactured, wherein the total weight percent of antioxidant present in the blend is less than or equal to 0.1 wt. %, based on the total weight of the polymer and the antioxidant. It is preferred that the antioxidant is one or more of: a) a phenolic antioxidant having a melting point greater than or equal to 60° C.; b) an aromatic amine; c) a sterically hindered amine; d) a hydroxylamine; e) an amine oxide derivative; and f) a phosphite and/or phosphonite. In one embodiment, where the antioxidant is phenolic and not octadecyl 3-(3,5-di-tert-butyl-4-hydroxyphenyl)propionate and/or where the antioxidant is a phosphite and/or phosphonite, tris(2,4-di-tert-butylphenyl)phosphite is excluded.

In some embodiments, at least a portion of the inner surface 108 or 308 of the wall of the collection means 105 or 305, respectively, contains an antioxidant. In some embodiments, substantially all or all of the inner surface 108 or 308 of the wall of the collection means 105 or 305, respectively, contains an antioxidant. In one embodiment the antioxidant is one or more of: a) a phenolics having a melting point greater than or equal to 60° C.; b) an aromatic amine; c) a sterically hindered amine; d) a hydroxylamine; e) an amine oxide derivative; and f) less than or equal to 0.1 wt. %, 0.08 wt. %, 0.05 wt. %, or 0.02 wt. % phosphite and/or phosphonite based on the weight of the polymer and the antioxidant.

In some embodiments, the antioxidant on the inner surface 108 or 308 of the wall of the collection means 105 or 305, respectively, is produced by blending an antioxidant with a polymer to form a polymer composition from which vessel 100 or 302 is manufactured, wherein the antioxidant comprises one or more of: a) a phenolics having a melting point greater than or equal to 60° C.; b) an aromatic amine; c) a sterically hindered amine; d) a hydroxylamine; and e) an amine oxide derivative.

In some embodiments, the antioxidant on the inner surface 108 or 308 of the wall of the collection means 105 or 305, respectively, is produced by blending an antioxidant with a polymer to form a polymer composition from which vessel 100 or 302 is manufactured, wherein the antioxidant is present in the polymer composition at less than or equal to 0.1 wt. %, based on the total weight of the polymer and t antioxidant, and the antioxidant comprises one or more of: a) a phenolic having a melting point greater than or equal to 60° C.; b) an aromatic amine; c) a sterically hindered amine; d) a hydroxylamine; e) an amine oxide derivative; and f) a phosphite and/or phosphonite.

In some embodiments, the antioxidant on the inner surface 109 or 309 of the reservoir 110 or 310, respectively, is produced by blending an antioxidant with a polymer to form a polymer composition from which vessel 100 or 302 is manufactured, wherein the antioxidant is present in the polymer composition at less than or equal to 0.1 wt. %, based on the total weight of the polymer and the antioxidant, and the antioxidant comprises one or more of: a) a phenolic t other than octadecyl 3-(3,5-di-tert-butyl-4-hydroxyphenyl) propionate; b) an aromatic amine; c) a sterically hindered amine; d) a hydroxylamine; e) an amine oxide derivative;

and f) a phosphite and/or phosphonite other than tris(2,4-di-tert-butylphenyl)phosphite.

In some embodiments, the antioxidant on the inner surface 108 or 308 of the wall of the collection means 105 or 305, respectively, is produced by blending an antioxidant with a polymer to form a polymer composition from which vessel 100 or 302 is manufactured, wherein the antioxidant is present in the polymer composition at less than or equal to 0.1 wt. %, based on the total weight of the polymer and the antioxidant, and the antioxidant comprises one or more of: a) a phenolic antioxidant other than octadecyl 3-(3,5-di-tert-butyl-4-hydroxyphenyl)propionate; b) an aromatic amine; c) a sterically hindered amine; d) a hydroxylamine; e) an amine oxide derivative; and f) a phosphite and/or phosphonite other than tris(2,4-di-tert-butylphenyl)phosphite.

In some embodiments, at least a portion of the bottom surface of the 372 of the reservoir sealing means 370 contains an antioxidant. In some embodiments, substantially all or all of the bottom surface of the 372 of the reservoir sealing means 370 contains an antioxidant.

In some embodiments, in addition to any or all of the above attributes, the apparatus comprises a reservoir seal means, wherein the reservoir has a first inner surface and the reservoir seal means has a bottom surface, such that when the reservoir seal means is installed, the first inner surface and the bottom surface circumscribe a sealed reservoir chamber. Installation of the seal means reduces exposure of the sample to air and/or reduces movement of the sample in response to movement of the container.

In some embodiments, the antioxidant on the bottom surface of the 372 of the reservoir sealing means 370 comprises a polymer composition of a polymer and one or more of: a) a phenolic having a melting point greater than or equal to 60° C.; b) an aromatic amine; c) a sterically hindered amine; d) a hydroxylamine; e) an amine oxide derivative; and f) less than or equal to 0.1 wt. %, 0.08 wt. %, 0.05 wt. %, or 0.02 wt. % phosphite and/or phosphonite based on the weight of the polymer and the antioxidant.

In some embodiments, the antioxidant on the bottom surface of the 372 of the reservoir sealing means 370 is produced by blending an antioxidant with a polymer to form a polymer composition from which vessel 100 or 302 is manufactured, wherein the antioxidant comprises one or more of: a) a phenolic having a melting point greater than or equal to 60° C.; b) an aromatic amine; c) a sterically hindered amine; d) a hydroxylamine; and e) an amine oxide derivative. In on embodiment, the antioxidant is present in the polymer composition in an amount less than or equal to 0.1 wt. %, based on the total weight of the polymer and the antioxidant, and the antioxidant comprises one or more of: a) a phenolic having a melting point greater than or equal to 60° C.; b) an aromatic amine; c) a sterically hindered amine; d) a hydroxylamine; e) an amine oxide derivative; and f) a phosphite and/or phosphonite. In yet another embodiment, the polymer composition excludes octadecyl 3-(3,5-di-tert-butyl-4-hydroxyphenyl)propionate and tris(2,4-di-tert-butylphenyl)phosphite.

Fabrication of the Apparatus

Fabrication of the components of the apparatus is generally performed by known methods such as, but not limited to, injection molding and blow molding. In some embodiments, these general methods further include steps and/or conditions that lead to one or more of the inner surface of the reservoir, the inner surface of the collection means, the inner surface of the lid, and or the inner surface of the reservoir seal means 370 containing antioxidants as described elsewhere in this disclosure.

In some embodiments, the first vessel 102 or 300 is manufactured from a mixture of polymer, preferably a thermoplastic and an antioxidant in an injection molding process under conditions. In some embodiments, the first vessel 102 or 300 is manufactured from a mixture of thermoplastic(s) and antioxidant(s) in a blow molding process under conditions appropriate for the selected thermoplastic. In some embodiments, the reservoir seal means 370 is manufactured from a mixture of thermoplastic(s) and antioxidant(s) in a blow molding process or an injection molding process under conditions appropriate for the selected thermoplastic. In an embodiment, the polymer composition comprises antioxidant(s) blended with a polymer in an amount less than or equal to 0.25 wt. %, less than or equal to 0.1 wt. %, less than or equal to 0.1 wt. %, less than or equal to 0.08 wt. %, or less than or equal to 0.05 wt. %. based on the total weight percent of the polymer and antioxidant.

Antioxidants

In some embodiments, the antioxidant is selected from one or more of phenolics, aromatic amines, sterically hindered amines, hydroxylamines, phosphites, and phosphonites.

Phenolic Antioxidants

The key reaction in the stabilization of polyolefins by phenolic antioxidants is the formation of hydroperoxides by transfer of a hydrogen from the phenolic moiety to the peroxy-radical resulting in the phenoxyl-radical. The steric hindrance by substituents, e.g. tert-butyl groups in the 2 and/or 6-position, influences the stability of the phenoxyl-radical or the mesomeric cyclohexadienonyl-radicals. Sterically hindered phenols can be classified according to the substituents' 2-, 4-, and 6-position.

Sterically hindered phenols are capable of preventing the abstraction of a hydrogen from the polymer backbone. The reactivity of the formed phenoxyl radical is significantly influenced by the substituents in 2- and 6-position. Bulky substituents prevent the reaction of the phenoxyl radical with the polymer and suppress dimerization of two phenoxyl radicals.

In some embodiments, phenolic antioxidants are selected from alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-ioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

In some embodiments, phenolic antioxidants are selected from alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

In some embodiments, phenolic antioxidants are selected from hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl- 4-hydroxyanisole, 3,5-di-tert-butyl-4-hydroxyphenyl stearate, bis-(3,5-di-tert-butyl-4-hydroxyphenyl)adipate.

In some embodiments, phenolic antioxidants are selected from tocopherols, for example α-tocopherol, β-tocopherol, γ-tocopherol, δ-tocopherol and mixtures thereof (Vitamin E).

In some embodiments, phenolic antioxidants are selected from hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl) disulfide.

In some embodiments, phenolic antioxidants are selected from alkylidenebisphenols, for example 2,2'-methylenebis (6-tert-butyl-4-methylphenol), 2,2'-methylenebis(6-tert-butyl-4-ethylphenol), 2,2'-methylenebis [4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

In some embodiments, phenolic antioxidants are selected from O-, N- and S-benzyl compounds, for example 3,5,3=, 5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

In some embodiments, phenolic antioxidants are selected from hydroxybenzylated malonates, for example dioctadecyl-2,2-bis-(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis-(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

In some embodiments, phenolic antioxidants are selected from aromatic hydroxybenzyl compounds, for example 1,3,5-tris-(3,5-di-tert-butyl-4-hydroxybenzyl)-2,4,6-trimethyl-benzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

In some embodiments, phenolic antioxidants are selected from triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

In some embodiments, phenolic antioxidants are selected from benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

In some embodiments, phenolic antioxidants are selected from acylaminophenols, for example 4-hydroxylauranilide, 4-hydroxystearanilide, octyl N-(3,5-di-tert-butyl-4-hydroxyphenyl)carbamate.

In some embodiments, phenolic antioxidants are selected from esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trim ethylolpropane, 4-hydroxymethyl-1-phospha-2,6,7-trioxabicyclo [2.2.2]octane.

In some embodiments, phenolic antioxidants are selected from esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trim ethylolpropane, 4-hydroxymethyl-1-phospha-2,6,7-trioxabicyclo [2.2.2]octane.

In some embodiments, phenolic antioxidants are selected from esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethyl hexane diol, trimethylolpropane, 4-hydroxymethyl-1-phospha-2,6,7-trioxabicyclo[2.2.2]octane.

In some embodiments, phenolic antioxidants are selected from esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

In some embodiments, phenolic antioxidants are selected from amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard® XL-1 supplied by Uniroyal).

In some embodiments, phenolic antioxidants are selected from ascorbic acid (vitamin C).

In some embodiments, phenolic antioxidants are selected from aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyl diphenyl amines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazin, N,N,N,N'-tetraphenyl-1,4-diaminobut-2-ene, N,N-bis(2,2,6,6-tetramethyl-piperid-4-yl-hexamethylene di amine, bis(2,2,6,6-tetramethylpiperid4-yl)sebacate, 2,2,6,6-tetramethylpiperidin-4-one, 2,2,6,6-tetramethylpiperidin-4-ol.

In some embodiments, a phenolic antioxidant when used alone as an antioxidant is used in amounts of up to and including 0.05 wt. %, 0.08 wt. %, 0.10 wt. %, or 0.25 wt. %, based on the total weight of the polymer to be stabilized and antioxidant. In some embodiments, one or more phenolic antioxidants when used in combination with one or more other antioxidants is used in amounts where the total of all antioxidants added to a polymer is up to and including 0.05 wt. %, 0.08 wt. %, 0.10 wt. %, or 0.25 wt. %, based on the total weight of the polymer to be stabilized and antioxidant. In some embodiments, the phenolic antioxidant excludes octadecyl 3-(3,5-di-tert-butyl-4-hydroxyphenyl)propionate.

Aromatic Amines

Secondary aromatic amines, and particularly aromatic diamines, are extremely efficient H-donors. The primary reaction products can subsequently react like the phenols in further transformation steps forming various coupling products.

In some embodiments, an aromatic amine when used alone as an antioxidant is used in amounts of up to and including 0.05 wt. %, 0.08 wt. %, 0.10 wt. %, or 0.25 wt. %, based on the total weight of the polymer to be stabilized and antioxidant. In some embodiments, on or more aromatic amines when used in combination with one or more other antioxidants is used in amounts where the total of all antioxidants added to a polymer is up to and including 0.05 wt. %, 0.08 wt. %, 0.10 wt. %, or 0.25 wt. %, based on the total weight of the polymer to be stabilized and antioxidant.

Sterically Hindered Amines

Sterically hindered amines are effective stabilizers against thermal degradation of polyolefins. The activity of these amines as antioxidants is based on their ability to form nitroxyl radicals. The reaction rate of nitroxyl radicals with alkyl radicals appears to be only slightly lower than that of alkyl radicals with oxygen. For this reason, nitroxyl radicals are efficient alkyl radical scavengers.

In some embodiments, hindered amines are at least one compound that contains at least one group of the formula (VI)

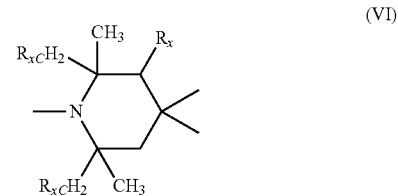

in which $R_x$ is hydrogen or methyl. Preferably $R_x$ is hydrogen. Preferably, compounds of component (c) are of high molecular weight and may be discrete compounds or oligomeric mixtures.

The compounds of the sterically hindered amine type, are known and some are commercially available.

Tinuvin™ and Chimassorb™ is available from BASF. Sanduvor™ and Hostavin™ is available from Clariant. Cyasorb™ is available from Solvay. Uvinul™ is available from BASF. Uvasil™ is available from Enichem. Uvasorb™ is available from 3V Sigma. BLS 1770 is Bis (2,2,6,6-tetramethyl-4-piperidyl) sebacate, available from Mayzo. Tinuvin™ 770 is Bis (2,2,6,6-tetramethyl-4-piperidyl) sebacate, available from BASF.

In some embodiments, a hindered amine when used alone as an antioxidant is used in amounts of up to and including 0.05 wt. %, 0.08 wt. %, 0.10 wt. %, or 0.25 wt. %, based on the total weight of the polymer to be stabilized and antioxidant. In some embodiments, on or more hindered amines when used in combination with one or more other antioxidants is used in amounts where the total of all antioxidants combined with a polymer is up to and including 0.05 wt. %, 0.08 wt. %, 0.10 wt. %, or 0.25 wt. %, based on the total weight of the polymer to be stabilized and antioxidant.

Hydroxylamines

Hydroxylamines can contribute in various ways to the stabilization of polymers. The reactive species is the intermediary nitrone which is capable of scavenging C-radicals under oxygen-deficient conditions. Such nitrones are active antioxidants.

The hydroxylamine derivatives of component i.) employed in the novel process are of the formula (II)

(II)

wherein $T_1$ is straight or branched chain alkyl of 1 to 36 carbon atoms, cycloalkyl of 5 to 12 carbon atoms, aralkyl of 7 to 9 carbon atoms, or said aralkyl substituted by one or two alkyl of 1 to 12 carbon atoms or by one or two halogen atoms;

$T_2$ is hydrogen, or independently has the same meaning as $T_1$.

In some embodiments, the hydroxylamine is selected from N,N-dihydrocarbylhydroxylamines of formula (II) wherein T1 and T2 are independently benzyl, ethyl, octyl, lauryl, dodecyl, tetradecyl, hexadecyl, heptadecyl or octadecyl, or wherein T1 and T2 are each the alkyl mixture found in hydrogenated tallow amine.

In some embodiments, the hydroxylamine is selected from N,N-dihydrocarbylhydroxylamines selected from the group consisting of N,N-dibenzylhydroxylamine, N,N-diethylhydroxylamine, N,N-dioctylhydroxylamine, N,N-dilaurylhydroxylamine, N,N-didodecylhydroxylamine, N,N-ditetradecylhydroxylaamine, N,N-dihexadecylhydroxylamine, N,N-dioctadecylhydroxylamine, N-hexadecyl-N-tetradecylhydroxylamine, N-hexadecyl-N-heptadecylhydroxylamine, N-hexadecyl-N-octadecylhydroxylamine, N-heptadecyl-N-octadecylhydroxylamine, and N,N-di(hydrogenated tallow)hydroxylamine.

In some embodiments, the hydroxylamine is selected from an N,N-di(alkyl)hydroxylamine produced by the direct oxidation of N,N-di(hydrogenated tallow)amine (Irgastab™ 042, Ciba Specialty Chemicals Corp.).

In some embodiments, a hydroxylamine when used alone as an antioxidant is used in amounts of up to and including 0.05 wt. %, 0.08 wt. %, 0.10 wt. %, or 0.25 wt. %, based on the total weight of the polymer to be stabilized and antioxidant. In some embodiments, one or more hydroxylamines when used in combination with one or more other antioxidants is used in amounts where the total of all antioxidants added to a polymer is up to and including 0.05 wt. %, 0.08 wt. %, 0.10 wt. %, or 0.25 wt. %, based on the total weight of the polymer to be stabilized and antioxidant.

Amine Oxide Derivatives

The amine oxide derivatives are saturated tertiary amine oxides as represented by general formula (III):

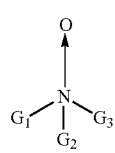
(III)

wherein $G_1$ and $G_2$ are independently a straight or branched chain alkyl of 6 to 35 carbon atoms, aryl of 6 to 12 carbon atoms, aralkyl of 7 to 36 carbon atoms, alkaryl of 7 to 36 carbon atoms, cycloalkyl of 5 to 36 carbon atoms, alkcycloalkyl of 5 to 36 carbon atoms or cycloalkylalkyl of 6 to 36 carbon atoms;

$G_3$ is a straight or branched chain alkyl of 1 to 35 carbon atoms, aryl of 6 to 12 carbon atoms, aralkyl of 7 to 36 carbon atoms, alkaryl of 7 to 36 carbon atoms, cycloalkyl of 5 to 36 carbon atoms, alkcycloalkyl of 6 to 36 carbon atoms or cycloalkylalkyl of 6 to 36 carbon atoms; with the proviso that at least one of $G_1$, $G_2$ and $G_3$ contains a β carbon-hydrogen bond; and wherein said alkyl, aralkyl, alkaryl, cycloalkyl, alkcycloalkyl and cycloalkylalkyl groups may be interrupted by one to sixteen —O—, —S—, —SO—, —SO$_2$—, —COO—, —OCO—, —CO—, —NG$_4$-, —CONG$_4$- and —NG$_4$CO— groups, or wherein said alkyl, aralkyl, alkaryl, cycloalkyl, alkcycloalkyl and cycloalkylallyl groups may be substituted by one to sixteen groups selected from —OG$_4$-, —SG$_4$, —COOG$_4$, —OCOG$_4$, —COG$_4$, —N(G$_4$)$_2$, —CON(G$_4$)$_2$, —NG$_4$COG$_4$ and 5- and 6-membered rings containing the —C(CH$_3$)(CH$_2$R$_x$)NL(CH$_2$R$_x$)CH$_3$)C— group or groups are both interupted and substituted by the groups mentioned above; and wherein $G_4$ is independently hydrogen or alkyl of 1 to 8 carbon atoms;

$R_x$ is hydrogen or methyl, preferably hydrogen;

L is a $C_{1-30}$ straight or branched chain alkyl moiety, a —C(O)R moiety wherein R is a $C_{1-30}$ straight or branched chain alkyl group, or a —OR moiety wherein R is a $C_{1-30}$ straight or branched chain alkyl group; and wherein said aryl groups may be substituted by one to three halogen, alkyl of 1 to 8 carbon atoms, alkoxy of 1 to 8 carbon atoms or combinations thereof.

A preferred structure of formula (III) is where $G_1$ and $G_2$ are independently benzyl or substituted benzyl. It is also possible for each of $G_1$, $G_2$, and $G_3$ to be the same residue. $G_1$ and $G_2$ are also preferably alkyl groups of 8 to 26 carbon atoms and most preferably alkyl groups of 10 to 26 carbon atoms and $G_3$ is preferably an alkyl group of 1 to 22 carbon atoms and most preferably methyl or substituted methyl. Also, preferred amine oxides include those wherein $G_1$, $G_2$, and $G_3$ are the same alkyl groups of 6 to 36 carbon atoms. Preferably, all of the aforementioned residues for $G_1$, $G_2$, and $G_3$ are saturated hydrocarbon residues or saturated hydrocarbon residues containing at least one of the aforementioned —O—, —S—, —SO—, —CO$_2$—, —CO—, or —CON— moieties. Those skilled in the art will be able to envision other useful residues for each of $G_1$, $G_2$, and $G_3$ without detracting from the present invention.

The saturated amine oxides of component ii.) may also include poly(amine oxides). By poly(amine oxide) is meant tertiary amine oxides containing at least two tertiary amine oxides per molecule. Illustrative poly(amine oxides), also called "poly(tertiary amine oxides)", include the tertiary amine oxide analogues of aliphatic and alicyclic diamines such as, for example, 1,4-diaminobutane; 1,6-diaminohexane; 1,10-diaminodecane; and 1,4-diaminocyclohexane, and aromatic based diamines such as, for example, diamino anthraquinones and diaminoanisoles.

Also included are tertiary amine oxides derived from oligomers and polymers of the aforementioned diamines. Useful amine oxides also include amine oxides attached to polymers, for example, polyolefins, polyacrylates, polyesters, polyamides, polystyrenes, and the like. When the amine oxide is attached to a polymer, the average number of amine oxides per polymer can vary widely as not all polymer chains need to contain an amine oxide. All of the aforementioned amine oxides may optionally contain at least one —O—, —S—, —SO—, —$CO_2$—, —CO—, or —$CONG_4$- moiety. In a preferred embodiment, each tertiary amine oxide of the polymeric tertiary amine oxide contains a C1 residue.

The groups $G_1$, $G_2$ and $G_3$ of formula (III) may be attached to a molecule containing a hindered amine. Hindered amines are known in the art and the amine oxide of the present invention may be attached to the hindered amine in any manner and structural position of the hindered amine. Useful hindered amines when part of a compound of component ii.) include those of the general formulas (IV) and (V):

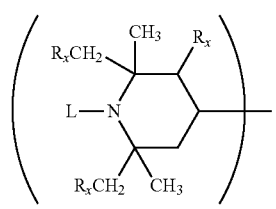

(IV)

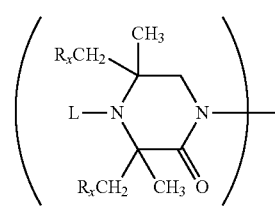

(V)

wherein L and $R_x$ are as described above. Also included are amine oxides containing more than one hindered amine and more than one saturated amine oxide per molecule. The hindered amine may be attached to a poly(terdary amine oxide) or attached to a polymeric substrate, as discussed above.

In some embodiments, an amine oxide derivative when used alone as an antioxidant is used in amounts of up to and including 0.05 wt. %, 0.08 wt. %, 0.10 wt. %, or 0.25 wt. %, based on the total weight of the polymer to be stabilized and antioxidant. In some embodiments, on or more amine oxide derivatives when used in combination with one or more other antioxidants is used in amounts where the total of all antioxidants added to a polymer is up to and including 0.05 wt. %, 0.08 wt. %, 0.10 wt. %, or 0.25 wt. %, based on the total weight of the polymer to be stabilized and antioxidant.

Phosphites and Phosphonites

Organophosphorus compounds of trivalent phosphorus are efficient hydroperoxide decomposers. A hydroperoxide reacts exactly stoichiometrically forming the corresponding alcohol, simultaneously oxidizing the phosphite to the corresponding phosphate. Because phosphites and phosphonites tend to hydrolyze, in practice mainly hydrolysis stable derivatives are being used. These are based generally on sterically hindered phenols. Because of their high reactivity, phosphites and phosphonites are used as stabilizers during processing in the melt (temperatures up to 300° C.).

Organic phosphites and phosphonites can be selected from the formulae (1), (2), (3), (4), (5), (6) and (7).

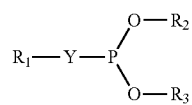

(1)

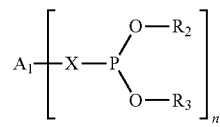

(2)

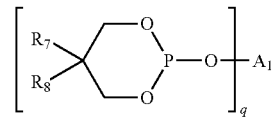

(3)

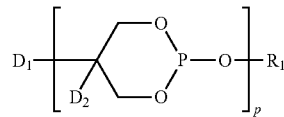

(4)

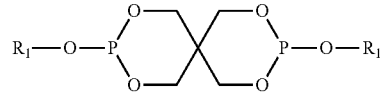

(5)

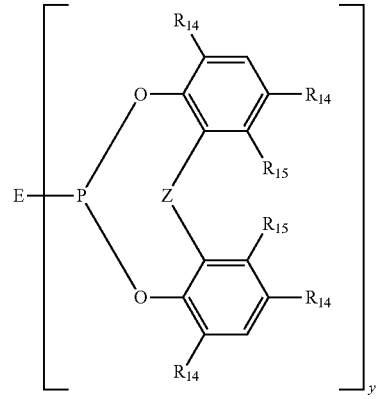

(6)

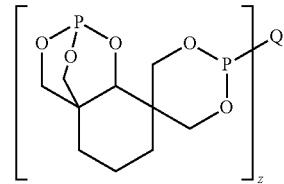

(7)

in which the indices are integral and n is 2, 3 or 4; p is 1 or 2, q is 2 or 3, r is 4 to 12; y is 1,2 or 3; and Z is 1 to 6;

$A_1$ if n is 2, is $C_2$-$C_{18}$ alkylene; $C_2$-$C_{12}$ alkylene interrupted by oxygen, sulfur or —$NR_4$—; a radical of the formula:

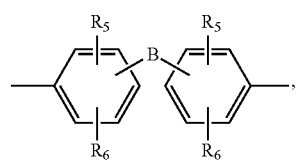

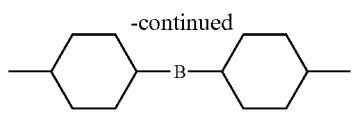

or
phenylene, $A_1$ if n is 3, is a radical of the formula $-C_rH_{2r-1}-$,
$A_1$ if n is 4, is

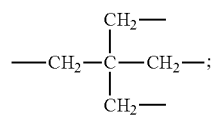

$A_2$ is as defined for $A_1$ if n is 2,
B is a direct bond, $-CH_2-$, $-CHR_4-$, $-CR_1R_4$, sulfur, $C_5-C_7$ cycloalkylidene, or cyclohexylidene which is substituted by from 1 to 4 $C_1-C_4$ alkyl radicals in position 3, 4 and/or 5,
$D_1$, if p is 1, is $C_1-C_4$ alkyl and, if p is 2, is $-CH_2OCH_2-$;
$D_2$, if p is 1, is $C_1-C_4$ alkyl,
E, if y is 1, is $C_1-C_{18}$ alkyl, $-OR_1$ or halogen;
E, if y is 2, is $-O-A_2-O-$,
E, if y is 3, is a radical of the formula $R_4C(CH_2O-)$ or $N(CH_2CH_2-O-)$;
Q is the radical of an at least Z-Valent alcohol or phenol, this radical being attached via the oxygen atom to the phosphorus atom;
$R_1R_2$ and $R_3$ independently of one another are $C_1-C_{18}$ alkyl which is unsubstituted or substituted by halogen, $-COOR_4$, $-CN$ or $-CONR_4R_4$, $C_2-C_{18}$ alkyl interrupted by oxygen, Sulfur or $-NR_4-$; $C_7-C_9$ phenylalkyl, $C_5-C_{12}$ cycloalkyl, phenyl or naphthyl, naphthyl or phenyl Substituted by halogen, 1 to 3 alkyl radicals or alkoxy radicals having a total of 1 to 18 carbon atoms or by $C_7-C_9$ phenylalkyl, or a radical of the formula

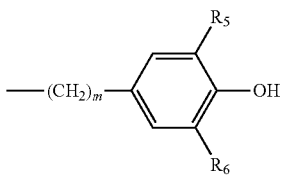

in which m is an integer from the range 3 to 6;
$R_4$ is hydrogen, $C_1-C_{18}$ alkyl, $C_5-C_{12}$ cycloalkyl or $C_7-C_9$ phenylalkyl,
$R_5$ and $R_6$ independently of one another are hydrogen, $C_1-C_8$ alkyl or $C_5-C_6$ cycloalkyl,
$R_7$ and $R_8$, if q is 2, independently of one another are $C_1-C_4$ alkyl or together are a 2,3-dehydropentamethylene radical; and
$R_7$ and $R_8$, if q is 3, are methyl,
$R_{14}$ is hydrogen, $C_1-C_9$ alkyl or cyclohexyl,
$R_{15}$ is hydrogen or methyl and, if two or more radicals $R_{14}$ and $R_{15}$ are present, these radicals are identical or different,
X and Y are each a direct bond or oxygen,
Z is a direct bond, methylene, $-C(R_{16})_2-$ or sulfur, and
$R_{16}$ is $C_1-C_8$ alkyl.

In one embodiment, at least one antioxidant is selected from the formulae (1), (2), (5) and (6), in which
n is the number 2, and y is the number 1, 2 or 3;
$A_1$ is $C_2-C_{18}$ alkylene, p-phenylene or p-biphenylene,
E, if y is 1, is $C_1-C_{18}$ alkyl, $-OR_1$ or fluorine;
E, if y is 2, is p-biphenylene,
E, if y is 3, is $N(CH_2CH_2O-)_3$,
$R_1$, $R_2$ and $R_3$ independently of one another are $C_1-C_{18}$ alkyl, $C_7-C_9$ phenylalkyl, cyclohexyl, phenyl, or phenyl substituted by 1 to 3 alkyl radicals having a total of 1 to 18 carbon atoms;
$R_{14}$ is hydrogen or $C_1-C_9$ alkyl,
$R_{15}$ is hydrogen or methyl,
X is a direct bond,
Y is oxygen,
Z is a direct bond or $-CH(R_{16})-$, and
$R_{16}$ is $C_1-C_4$ alkyl.

In yet another embodiment, the antioxidant is selected from the formulae (1), (2), (5) and (6), in which
n is the number 2 and y is the number 1 or 3;
$A_1$ is p-biphenylene,
E, if y is 1, is $C_1-C_{18}$ alkoxy or fluorine,
E, if y is 3, is $N(CH_2CH_2O-)$,
$R_1$, $R_2$ and $R_3$ independently of one another are $C_1-C_8$ alkyl, or phenyl substituted by 2 or 3 alkyl radicals having a total of 2 to 12 carbon atoms,
$R_{14}$ is methyl or tert-butyl,
$R_{15}$ is hydrogen;
X is a direct bond;
Y is oxygen; and
Z is a direct bond, methylene or $-CH(CH_3)-$.

In one particularly preferred embodiment, the antioxidant is selected from the formulae (1), (2) and (6).

In a preferred embodiment, the antioxidant is of the formula (I)

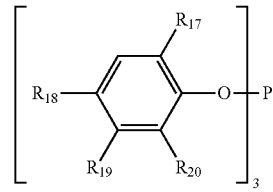

in which
$R_{17}$ and $R_{18}$ independently of one another are hydrogen, $C_1-C_8$ alkyl, cyclohexyl or phenyl, and
$R_{19}$ and $R_{20}$ independently of one another are hydrogen or $C_1-C_4$ alkyl.

In some embodiments, organic phosphites and phosphonites are selected from triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl)phosphite (Irgafos® 168, Ciba Specialty Chemicals Corp.), diisodecyl pentaerythritol diphosphite, bis(2,4-di-tert-butylphenyl)pentaerythritol diphosphite (formula (D)), bis(2,6-di-tert-butyl-4-methylphenyl)pentaerythritol diphosphite (formula (E)), bisisodecyloxypentaerythritol diphosphite, bis(2,4-di-tert-butyl-6-methylphenyl)pentaerythritol diphosphite, bis(2,4,6-tri-tert-butylphenyl)pentaerythritol diphosphite, tristearyl sorbitol triphosphite, tetrakis-(2,4-di-tert-butylphenyl)4,4'-biphenylene-diphosphonite (Irgafos® P-EPQ, Ciba Specialty Chemicals Corp., formula (H)), 6-isooctyloxy-2,4,8,10-tetra-tert-butyldibenzo[d,f][1,3,2]dioxaphosphepin), 6-fluoro-2,4,8,10-tetra-tert-butyl-12-methyldibenzo[d,g] [1,3,2]dioxaphosphocin), bis(2,4-di-tert-butyl-6-methylphenyl)methyl phosphite, bis(2,4-di-tert-butyl-6-methylphenyl)ethyl phosphite.

In some embodiments, phosphites and phosphonites are selected from tris(2,4-di-tert-butylphenyl)phosphite (Irgafos™ 168, Ciba Specialty Chemicals Corp.), tris(nonylphenyl)phosphite, bis(2,4-di-tert-butyl-6-methylphenyl) ethyl phosphite (Irgafos™ 38, Ciba Specialty Chemicals Corp.), bis(2,4-di-tert-butylphenyl)pentaerythritol diphosphite (Ultranox™ 626, Addivant), tetrakis(2,4-di-tert-butylphenyl)4,4'-biphenylenediphosphonite (Irgafos™ P-EPQ, Ciba Specialty Chemicals Corp.), 2,2',2"-nitrilo [triethyltris(3,3'5,5'-tetra-tert-butyl-1,1'-biphenyl-2,2'-diyl) phosphite] (Irgafos™ 12, Ciba Specialty Chemicals Corp.). Ultranox™ 641 (Addivant), Doverphos™ S9228 (Dover Chemicals) or Mark® HP10 (Adeka Argus).

In some embodiments, a phosphite and/or phosphonite when used alone as an antioxidant is used in amounts of up to and including 0.05 wt. %, 0.08 wt. %, 0.10 wt. %, or 0.25 wt. %, based on the total weight of the polymer to be stabilized and antioxidant. In some embodiments, on or more phosphite and/or phosphonites when used in combination with one or more other antioxidants is used in amounts where the total of all antioxidants added to a polymer is up to and including 0.05 wt. %, 0.08 wt. %, 0.10 wt. %, or 0.25 wt. %, based on the total weight of the polymer to be stabilized and antioxidant. In some embodiments, a phosphite and/or phosphonite excludes tris(2,4-di-tert-butylphenyl)phosphite.

Compositions

In some embodiments, a polymer composition is provided comprising a blend of a thermoplastic suitable for injection molding and an antioxidant, wherein the blend is subjected to injection molding conditions and then cooled to produce a solid material having a surface comprising the antioxidant in an amount sufficient to mitigate oxidative damage to biological fluids. The antioxidant is selected from one of more of: a) a phenolic other than octadecyl 3-(3,5-di-tert-butyl-4-hydroxyphenyl)propionate; b) an aromatic amine; c) a sterically hindered amine; d) a hydroxylamine; e) an amine oxide derivative; and f) a phosphite and/or phosphonite other than tris(2,4-di-tert-butylphenyl)phosphite.

Medical Devices

In some embodiments, a medical device is provided for collecting, storing, and/or processing biological fluids, the apparatus comprising at least one component having a surface to which the biological fluid will be contacted, wherein the surface comprises an antioxidant in an amount sufficient to mitigate oxidative damage to biological fluids. The antioxidant is selected from one of more of: a) a phenolic other than octadecyl 3-(3,5-di-tert-butyl-4-hydroxyphenyl)propionate; b) an aromatic amine; c) a sterically hindered amine; d) a hydroxylamine; e) an amine oxide derivative; and f) a phosphite and/or phosphonite other than tris(2,4-di-tert-butylphenyl)phosphite.

Various embodiments of the invention include, but are not limited to:

(a) In some embodiments, an apparatus comprises a first vessel comprising a collection means at the upper end of the first vessel; and a reservoir at the lower end of the first vessel, the reservoir having a first inner surface. The first inner surface comprises a first antioxidant comprising a phenolic antioxidant, an aromatic amine, a sterically hindered amine, a hydroxylamine, a phosphite, phosphonites, or combinations thereof (b) In some embodiments of the apparatus, in addition to the attributes of paragraph (a), the phenolic antioxidant has one or more of a molecular weight greater than or equal to 600, a melting temperature greater than or equal to 60° C., and a linear molecular structure substantially free of sidechains.

(c) In some embodiments, in addition to the attributes of paragraphs (a)-(b), the apparatus further comprises a lid suited for sealable attachment to the first vessel.

(d) In some embodiments, in addition to the attributes of paragraphs (a)-(c), the apparatus further a reservoir seal means.

(e) In some embodiments, in addition to the attributes of paragraphs (a)-(d), the apparatus further comprises a second vessel, wherein the first vessel is inserted into the second vessel.

(f) In some embodiments, in addition to the attributes of paragraph (a)-(e), the first inner surface comprises geometric surface features suited to increase the ratio of the area of the first inner surface to the volume.

(g) In some embodiments, in addition to the attributes of paragraphs (e)-(f), the first vessel, the second vessel, the reservoir seal means, and the lid are each independently comprised of acrylonitrile butadiene styrene, polyamide, polybutylene terephthalate, polycaprolactam, polycarbonate, polyether ether ketone, polyetherimide, polyethylene, polyethylene terephthalate, polymethyl methacrylate, polyoxymethylene, polyphenylene sulfide, polyphenylsulfone, polypropylene, polystyrene, polyvinylidene fluoride, styrene acrylonitrile resin, thermoplastic elastomers, thermoplastic polyurethane, or combinations thereof (h) In some embodiments, in addition to the attributes of paragraphs (a)-(g), the first antioxidant is chemically and/or physically bonded to the first inner surface in any manner effective to produce active antioxidant species on the surface. Methods to accomplish this include but are not limited to blending an antioxidant into a polymer from which the vessel is formed, laminating a antioxidant-containing film to the surface (either thermally or by adhesive), by extrusion of an antioxidant-containing polymer onto the surface, or by dissolving a polymer in a solvent along with an antioxidant, applying the solvent to the target surface and evaporating the solvent to leave an adhered polymer film layer.

(i) In some embodiments, in addition to the attributes of paragraphs (a)-(h), the wherein the collection means has a third inner surface, wherein the third inner surface comprises a second antioxidant comprising a phenolic antioxidant, an aromatic amine, a sterically hindered amine, a hydroxylamine, a phosphite, phosphonites, or combinations thereof.

(j) In some embodiments, in addition to the attributes of paragraph (i), the phenolic antioxidant has one or more of a molecular weight greater than or equal to 600, a melting temperature greater than or equal to 60° C., and a linear molecular structure substantially free of sidechains.

(k) In some embodiments, in addition to the attributes of paragraphs (i)-(j), second antioxidant is chemically and/or physically bonded to the first inner surface in any manner effective to produce active antioxidant species on the surface. Methods to accomplish this include but are not limited to blending an antioxidant into a polymer from which the vessel is formed, laminating a antioxidant-containing film to the surface (either thermally or by adhesive), by extrusion of an antioxidant-containing polymer onto the surface, or by dissolving a polymer in a solvent along with an antioxidant, applying the solvent to the target surface and evaporating the solvent to leave an adhered polymer film layer.

(l) In some embodiments, in addition to the attributes of paragraphs (i)-(k), wherein the first and second antioxidant are the same or different.

(m) In some embodiments, an apparatus comprises a first vessel having a wall attached at its lower end to a reservoir and having a first edge at its upper end; and a support means suitable for maintaining the first vessel in an upright orientation; wherein the reservoir and the wall form a first inner surface circumscribing a chamber within the first vessel, and at least a portion of the first inner surface comprises an antioxidant comprising a phenolic antioxidant, an aromatic amine, a sterically hindered amine, a hydroxylamine, a phosphite, phosphonites, or combinations thereof.

(n) In some embodiments, a medical device is provided for collecting, storing, and/or processing biological fluids, the device comprising at least one component having a surface to which the biological fluid will be contacted, wherein the surface comprises an antioxidant in an amount sufficient to mitigate oxidative damage to biological fluids.

(o) In some embodiments, in addition to the attributes of paragraph (n), the medical device is provided wherein the antioxidant is selected from one of more of: a) a phenolic antioxidant other than octadecyl 3-(3,5-di-tert-butyl-4-hydroxyphenyl)propionate; b) an aromatic amine; c) a sterically hindered amine; d) a hydroxylamine; e) an amine oxide derivative; and f) a phosphite and/or phosphonite other than tris(2,4-di-tert-butylphenyl)phosphite.

(p) In some embodiments, in addition to the attributes of paragraph (n), the medical device is provided wherein the antioxidant is selected from one of more of: a) a phenolic antioxidant having a melting point greater than or equal to 60° C.; b) an aromatic amine; c) a sterically hindered amine; d) a hydroxylamine; and e) an amine oxide derivative.

(q) In some embodiments, in addition to the attributes of paragraph (n), the medical device is provided wherein the surface is formed by a blend of a polymer and less than or equal to 0.1 wt. % of a first antioxidant based on the weight of the blend, and the first antioxidant comprises one or more of: a) a phenolic antioxidant having a melting point greater than or equal to 60° C.; b) an aromatic amine; c) a sterically hindered amine; d) a hydroxylamine; e) an amine oxide derivative; and f) a phosphite and/or phosphonite.

(r) In some embodiments, in addition to the attributes of paragraph (n), the medical device is provided wherein the wherein the surface is formed by a blend of a polymer and a first antioxidant, the first antioxidant comprising one or more of: a) a phenolic antioxidant having a melting point greater than or equal to 60° C.; b) an aromatic amine; c) a sterically hindered amine; d) a hydroxylamine; e) an amine oxide derivative; and f) less than or equal to 0.1 wt. % of a phosphite and/or phosphonite, based on the weight of the blend.

(s) In some embodiments, in addition to the attributes of paragraphs (n)-(r), wherein the polymer is selected from acrylonitrile butadiene styrene, polyamide, polybutylene terephthalate, polycaprolactam, polycarbonate, polyether ether ketone, polyetherimide, polyethylene, polyethylene terephthalate, polymethyl methacrylate, polyoxymethylene, polyphenylene sulfide, polyphenylsulfone, polypropylene, polystyrene, polyvinylidene fluoride, styrene acrylonitrile resin, thermoplastic elastomers, thermoplastic polyurethane, or combinations thereof.

(t) In some embodiments, a composition comprises the reaction product of a blend of a polymer and an antioxidant suitable for injection molding, to make a product having a surface comprising an antioxidant in an amount sufficient to mitigate oxidative damage to biological fluids.

(u) In some embodiments, in addition to the attributes of paragraph (s) the composition is provided is provided wherein the antioxidant is selected from one of more of: a) a phenolic antioxidant other than octadecyl 3-(3,5-di-tert-butyl-4-hydroxyphenyl)propionate; b) an aromatic amine; c) a sterically hindered amine; d) a hydroxylamine; e) an amine oxide derivative; and f) a phosphite and/or phosphonite other than tris(2,4-di-tert-butylphenyl)phosphite.

(v) In some embodiments, in addition to the attributes of paragraph (s) the composition is provided wherein the antioxidant is selected from one of more of: a) a phenolic antioxidant having a melting point greater than or equal to 60° C.; b) an aromatic amine; c) a sterically hindered amine; d) a hydroxylamine; and e) an amine oxide derivative.

(w) In some embodiments, in addition to the attributes of paragraph (s), the composition is provided wherein the surface is formed by a blend of a polymer and less than or equal to 0.1 wt. % of a first antioxidant based on the weight of the blend, and the first antioxidant comprises one or more of: a) a phenolic antioxidant having a melting point greater than or equal to 60° C.; b) an aromatic amine; c) a sterically hindered amine; d) a hydroxylamine; e) an amine oxide derivative; and f) a phosphite and/or phosphonite.

(x) In some embodiments, in addition to the attributes of paragraph (s), the composition is provided wherein the wherein the surface is formed by a blend of a polymer and a first antioxidant, the first antioxidant comprising one or more of: a) a phenolic antioxidant having a melting point greater than or equal to 60° C.; b) an aromatic amine; c) a sterically hindered amine; d) a hydroxylamine; e) an amine oxide derivative; and f) less than or equal to 0.1 wt. % of a phosphite and/or phosphonite, based on the weight of the blend.

(y) In some embodiments, in addition to the attributes of paragraphs (s)-(w), wherein the polymer is selected from acrylonitrile butadiene styrene, polyamide, polybutylene terephthalate, polycaprolactam, polycarbonate, polyether ether ketone, polyetherimide, polyethylene, polyethylene terephthalate, polymethyl methacrylate, polyoxymethylene, polyphenylene sulfide, polyphenylsulfone, polypropylene, polystyrene, polyvinylidene fluoride, styrene acrylonitrile resin, thermoplastic elastomers, thermoplastic polyurethane, or combinations thereof.

(z) In some embodiments, a method for making an apparatus for collecting and/or storing semen comprises:
combining a thermoplastic and an antioxidant under heat sufficient to form a thermoplastic melt wherein the antioxidant comprises a phenolic antioxidant, an aromatic amine, a sterically hindered amine, a hydroxylamine, a phosphite, phosphonites, or combinations thereof;

injecting the thermoplastic melt into a vessel mold under injection molding conditions to form a vessel comprising the thermoplastic melt;

cooling the vessel; and removing from the mold a vessel having an inner surface comprising the antioxidant.

(aa) In some embodiments, in addition to the attributes of paragraph (z) the method is provided is provided wherein the antioxidant is selected from one of more of: a) a phenolic antioxidant other than octadecyl 3-(3,5-di-tert-butyl-4-hydroxyphenyl)propionate; b) an aromatic amine; c) a sterically hindered amine; d) a hydroxylamine; e) an amine oxide derivative; and f) a phosphite and/or phosphonite other than tris(2,4-di-tert-butylphenyl)phosphite.

(bb) In some embodiments, in addition to the attributes of paragraph (z), the method is provided wherein the antioxidant is selected from one of more of: a) a phenolic antioxidant having a melting point greater than or equal to 60° C.; b) an aromatic amine; c) a sterically hindered amine; d) a hydroxylamine; and e) an amine oxide derivative.

(cc) In some embodiments, in addition to the attributes of paragraph (z), the method is provided wherein the surface is formed by a blend of a polymer and less than or equal to 0.1 wt. % of a first antioxidant based on the weight of the blend, and the first antioxidant comprises one or more of: a) a phenolic antioxidant having a melting point greater than or equal to 60° C.; b) an aromatic amine; c) a sterically hindered amine; d) a hydroxylamine; e) an amine oxide derivative; and f) a phosphite and/or phosphonite.

(dd) In some embodiments, in addition to the attributes of paragraph (z), the method is provided wherein the wherein the surface is formed by a blend of a polymer and a first antioxidant, the first antioxidant comprising one or more of: a) a phenolic antioxidant having a melting point greater than or equal to 60° C.; b) an aromatic amine; c) a sterically hindered amine; d) a hydroxylamine; e) an amine oxide derivative; and f) less than or equal to 0.1 wt. % of a phosphite and/or phosphonite, based on the weight of the blend.

(ee) In some embodiments, in addition to the attributes of paragraphs (z)-(dd), wherein the polymer is selected from acrylonitrile butadiene styrene, polyamide, polybutylene terephthalate, polycaprolactam, polycarbonate, polyether ether ketone, polyetherimide, polyethylene, polyethylene terephthalate, polymethyl methacrylate, polyoxymethylene, polyphenylene sulfide, polyphenylsulfone, polypropylene, polystyrene, polyvinylidene fluoride, styrene acrylonitrile resin, thermoplastic elastomers, thermoplastic polyurethane, or combinations thereof.

(ff) An apparatus comprising a first vessel having a collection means at the upper end of the first vessel and a reservoir at the lower end of the first vessel, wherein the first vessel is formed from a blend of a polymer and an antioxidant, the antioxidant comprising one or more of: a) a phenolic other than octadecyl 3-(3,5-di-tert-butyl-4-hydroxyphenyl)propionate; b) an aromatic amine; c) a sterically hindered amine; d) a hydroxylamine; e) an amine oxide derivative; and f) a phosphite and/or phosphonite other than tris(2,4-di-tert-butylphenyl)phosphite.

The following examples illustrate the invention; however, those skilled in the art will recognize numerous variations within the spirit of the invention and scope of the claims. To facilitate a better understanding of the present invention, the following examples of preferred embodiments are given. In no way should the following examples be read to limit, or to define, the scope of the invention.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

I. STARTING MATERIALS

A. Antioxidants

Antioxidant used in polymers and films in the examples were:

| Label herein | Commercial name | Description | Available from |
|---|---|---|---|
| A1 | Tinuvin ™ 622 | oligomeric hindered amine light stabilizer ("HALS") | BASF Corporation, Houston, Texas |
| A2 | Chimassorb ™ 944 | high molecular weight hindered amine light stabilizer ("HALS") | BASF Corporation, Houston, Texas |
| A3 | Irgafos ™ 168 | hydrolytically stable phosphite processing stabilizer | BASF Corporation, Houston, Texas |
| A4 | Irganox ™ 1010 | sterically hindered phenolic primary antioxidant | BASF Corporation, Houston, Texas |
| A5 | Irganox ™ 1076 | sterically hindered phenolic antioxidant | BASF Corporation, Houston, Texas |
| A6 | Mayzo ™ BLS 1770 | low molecular weight hindered amine light stabilizer | Mayzo, Inc., Suwanee, Gerogia |

B. Polymers

Polymers used for fabrication of ProteX™ and TrueBreed™ semen collection containers was Formalene™ 2610A Polypropylene Copolymer, available from Formosa Plastics Corporation, Point Comfort, Tex. Formalene™ 2610A Polypropylene Copolymer was determined to contain the following antioxidants: 457.1 ppm A5, 333.7 ppm A3 (oxidized), and 721.7 ppm A3 (unoxidized). Formalene™ 2610A Polypropylene Copolymer is labeled herein as "P1." In one embodiment of the invention, Formalene 2610A is excluded as a polymer and antioxidant in the polymer compositions of the invention. In yet another embodiment, the specific combination and amounts of A5 and A3 are excluded from the polymer composition useful for making the inventive apparatus, or the amount of A5 in the polymer composition of the invention is less than 0.1 weight percent based on the total weight percent of the polymer in the polymer composition.

Polymer used for fabrication of inventive semen containers was Ineos™ R12C-01 Polypropylene Copolymer, available from Ineos Olefins & Polymers, League City, Tex. Ineos™ R12C-01 Polypropylene Copolymer was determined to contain: 274.0 ppm A4, 342.7 ppm A3 (oxidized), and 228.6 ppm A3 (unoxidized). Ineos™ R12C-01 Polypropylene Copolymer is labeled herein as "P2."

Polymer used for fabrication of film samples was Makrolon™ 2558 Polycarbonate, available from Covestro, South Deerfield, Mass. Makrolon™ 2558 Polycarbonate is labeled herein as "P3."

C. Containers

For human semen samples and bovine semen samples, baseline performance for containers typically used for collection of semen samples was determined using a standard semen collection cup (Fisher Brand Specimen Container #1632070, available from Thermo-Fisher, Pittsburgh, Pa.) and a ProteX™ semen collection container, available from Reproductive Solutions, Inc. in Dallas, Tex. The ProteX™ semen collection container in injection molded using polymer P1. The standard semen collection cup is labeled herein as "C1," and the ProteX™ semen collection container is labeled herein as "C2."

For equine semen samples, baseline performance for containers typically used for collection of semen samples was determined using standard baby bottle (Parent's Choice Baby Bottles, 9 fl. oz, available from Walmart, Inc, Bentonville, Ark.) and a TrueBreed™ semen collection container, available from Reproductive Solutions (house device), Inc. in Dallas, Tex. The TrueBreed™ semen collection container is injection molded using polymer P1. The standard semen collection cup is labeled herein as "C4," and the TrueBreed™ semen collection container ProteX™ container is labeled herein as "C5."

D. Media

Semen samples are mixed with media to preserve viability and minimize damage to the sperm during collection and storage. Media used in the examples were as follows:

| Label herein | Description | Available from |
|---|---|---|
| M1 | Multipurpose Handling Medium ("MHM") | FUJIFILM Irvine Scientific in Dallas, Texas |
| M2 | Ham's F-10 Liquid | FUJIFILM Irvine Scientific in Dallas, Texas |
| M3 | INRA 96 Equine semen extender and preservation media for fresh and cooled equine semen | IMV Technologies in Maple Grove, Minnesota |
| M4 | Multipurpose Handling Media-Complete ("MHM-C") | FUJIFILM Irvine Scientific in Dallas, Texas |

II. PREPARED MATERIALS

A. Containers

For human semen samples and bovine semen samples, inventive containers were fabricated using polymer P2. The containers were fabricated by injection molding using substantially the same molds and conditions as used for fabrication of the C2 containers. The inventive semen collection container used for human and bovine semen samples is labeled herein as "C3."

For equine semen samples, inventive containers were fabricated using polymer P2. The containers were fabricated by injection molding using substantially the same molds and conditions as used for fabrication of the C5 containers. The inventive semen collection container used for equine semen samples is labeled herein as "C6."

B. Films

Cast films used in the examples were prepared by dissolving the polycarbonate pellets and the corresponding additive, if applicable, in dichloro-methane solvent to effect a weight concentration solution of 15% polymer and 0.1% additive. This solution was then added to the surface of a glass plate and a film was prepared using a film applicator with a 0.0015" gap. After allowing the solvent to evaporate the film samples were removed from the glass and placed in an oven at a temperature of 50° C. for 60 minutes to drive off any residual solvent. Films used in polymers in the examples were:

| Film label herein | Polymer | Antioxidant |
|---|---|---|
| F1 | P3 | No added antioxidant |
| F2 | P3 | A1 |
| F3 | P3 | A2 |
| F4 | P3 | A3 |
| F5 | P3 | A4 |
| F6 | P3 | A6 |

III. EQUIPMENT

Prepared semen samples were analyzed for sperm movement or kinematics using a Hamilton Thorne IVOS computer assisted semen analyzer ("CASA"), available from Hamilton Thorne in Beverly, Mass. (Version 12 software for IVOS).

Equipment used for gathering equine semen samples included a Missouri Artificial Vagina, available from IMV Technologies in Maple Grove, Minn.

Prepared human semen samples were analyzed for DNA integrity using a Halosperm™ G2 test kit, available from Spectrum Technologies in Healdsburg, Calif. and a standard saturated chlortetracycline technique.

Prepared equine semen samples were analyzed for DNA integrity using a Halosperm™ equine test kit, available from Spectrum Technologies in Healdsburg, Calif., and a standard saturated chlortetracycline technique.

Prepared bovine semen samples were analyzed for DNA integrity using a Halosperm™ bovine test kit, available from Spectrum Technologies in Healdsburg, Calif., and a standard saturated chlortetracycline technique.

IV. DEFINITIONS

When referring to cells/ml of media, cells means individual spermatozoa cells per milliliter of fluid.

Analysis of variance ("ANOVA") means a collection of statistical models and their associated estimation procedures (such as the "variation" among and between groups) used to analyze the differences among means.

Amplitude of lateral head or lateral displacement ("ALH"): Displacement corresponding to the mean width of the head oscillation as the sperm swims. Mean ALH is calculated from all cell tracks that have a straightness greater than the threshold STR and are not measured as SLOW. Measured using CASA.

Average pathway velocity or path velocity ("VAP"): Average velocity of the smoothed cell path in microns/second. Slow cells are excluded from the average. Measured using CASA.

Beat cross frequency ("BCF"): Frequency with which the sperm track crosses the sperm path (i.e., frequency of sperm head crossing the sperm average path in either direction). This value is measured in crossings per second (Hertz). A cell must not be slow to be included in the average. Measured using CASA.

Concentration: Sperm count per unit volume, typically million cells/ml (Mimi). Measured using CASA.

Elongation: Average value of the ratio of minor to major axis of all sperm heads.

Linearity ("LIN"): Average value of the ratio VSL/VCL. LIN measures the departure of the cell track from a straight line. Measured using CASA.

Manual volume measurement: Manual measurement entered into CASA.

Medium cells: Fraction of all cells moving with VAP cutoff<VAP<progressive cell VAP.

Mitochondrial intactness: Analyzed using a standard mitotracker red technique.

Morphology: The size and shape of sperm; examined as part of a semen analysis to evaluate male infertility. Sperm morphology results are reported as the percentage of sperm that appear normal when semen is viewed under a microscope. Analyzed using a rapid H&E staining technique.

Motility: Healthy sperm motility is defined as sperm with forward progressions of at least 25 micrometers per second, typically reported as percentage of total sperm that are "motile." Measured using CASA. Results of a donor are normalized against motility at collection time of that donor's sperm for comparison to other donors.

Progressive cells: Number of cells moving with both VAP>medium VAP cutoff and straightness STR>$S_0$.

Rapid cells: Percentage of motile cells with VAP>medium VAP cutoff. Measured using CASA. Results of a donor are normalized against rapid cells at collection time of that donor's sperm for comparison to other donors.

Slow cells: Fraction of all cells moving with VAP<VAP cutoff or VSL<VSL cutoff.

Straight-line velocity, progressive velocity, or progression ("VSL"): Average velocity measured in a straight line from the beginning to the end of track. Slow cells are excluded from the average. Measured using CASA.

Straightness ("STR"): Average value of the ratio VSL/VAP. STR measures the departure of the cell path from a straight line. Measured using CASA.

Track speed or curvilinear velocity ("VCL"): average velocity measured over the actual point-to-point track followed by the cell. Slow cells are excluded from the average. Measured using CASA.

V. REFERENCES

WHO laboratory manual for the Examination and processing of human semen, Fifth Ed., World Health Organization ("WHO Manual").

VI. EXPERIMENTAL METHODS

A. Semen Sample Collection and Treatment

Human, equine, and bovine semen samples were collected and analyzed according to the to the following methods.

1. Human Testing

Ten (10) donors were recruited that had normal semen parameters at testing using the WHO Manual for normal semen analysis. Each donor then supplied four (4) samples. Each of the four (4) samples from each donor was collected a minimum of three (3) days a maximum of seven (7) days after the previous sample and a minimum of three (3) days a maximum of seven (7) days before the following sample.

Treatment of samples was as follows:

| Treatment No. | Container | Media (one [1] ml) |
|---|---|---|
| H1 | C1 | M1 |
| H2 | C2 | M1 |
| H3 | C3 | M1 |
| H4 | C3 | M2 |

Donors were assigned randomly to which treatment they started, after which treatments proceeded in sequence. For example, if a donor was assigned to start with Treatment H3, subsequent samples were collected using Treatments H4, H1, and H2, in order.

Each sample was:
1) collected via masturbation into the designated container type (media was added to each container prior to collection of semen samples);
2) after collection, allowed to liquify for 10-30 minutes;
3) after liquification and manual volume measurement, using a CASA, analyzed for: concentration, motility, rapid cells, VAP, VSL, VCL, ALH, BCF, STR, and LIN;
4) then prepared using a standard sperm washing technique (as described in *Handbook of the Laboratory Diagnosis and Treatment of Infertility*, Keel and Webster. CRC Press, 1990); 5 ml instead of 0.5 ml to allow sufficient volume for experiment] by:
   a. adding 2 ml of additional media (same as originally in collection device),
   b. centrifuging at 600 RPM for 6 minutes, (Sorvall, Model RT 6000, DuPont Instruments)
   c. removing supernatant,
   d. adding 5 ml of media (same as originally in collection device),
   e. mixing sperm into media, [(vortexed for 10 seconds or until no obvious pellet)
   f. repeating CASA measurements at approximate times after collection of 1 hour, 3 hours, 6 hours, 9 hours, 12 hours, and 24 hours and incubating the cells at a temperature of 37° C. This process for each sample was terminated upon detection of remaining motility. Additionally, slides were prepared at each time point for analysis of morphology, mitochondrial intactness, and DNA.

2. Equine Testing

Semen samples collected from ten (10) healthy stallions. Three (3) samples were obtained from each stallion each week on a Monday-Wednesday-Friday schedule over two (2) weeks.

Treatment of samples was as follows:

| Treatment No. | Container | Media (ten [10] ml) |
|---|---|---|
| E1 | C4 | M3 |
| E2 | C5 | M3 |
| E3 | C6 | M3 |

Studs were assigned randomly to which treatment they started, after which treatments proceeded in sequence. For example, if a donor was assigned to start with Treatment E2, subsequent samples were collected using Treatments E3 and E1, in order.

Each sample was:
1) collected using a Missouri Artificial Vagina (media was added to each container prior to collection of semen samples.
2) manual volume measurement, using a CASA, analyzed for: concentration, motility, rapid cells, VAP, VSL, VCL, ALH, BCF, STR, and LIN;
3) further extended in a laboratory to a final concentrations of approximately (±10%) 20 million cells/ml;
4) repeating CASA analysis made on the fresh semen sample at approximately 6 hours, 9 hours, 12 hours, 24 hours, 48 hours, 72 hours, and 96 hours after collection and incubating the cells at room temperature. This process for each sample was terminated upon detection of remaining motility. Additionally, slides were prepared at each time point for analysis of morphology, mitochondrial intactness, and DNA.

3. Bovine Testing

In these examples, frozen bovine semen was thawed and processed similarly to intrauterine insemination ("IUI") samples. Sufficient quantities of semen from three (3) bulls were used to create three samples, each representing a single bull. Each of the three (3) sample suspensions contained 20-28 million cells/ml in fifteen (15) ml of Type 4 Media.

Cells were thawed and prepared using standard techniques (Straw is exposed to room air for 90 secs, plunged in a water bath for 2 minutes, transferred to a 12 ml styrene test tube (BD Falcon, St Louis, Mich.); standard wash, in Keel and Brooks, only deviation is final volume) and resuspended in 6 mL of Type 4 Media. Each sample was then tested for initial motility and rapid cell movement to allow normalization of these data for statistical analysis.

Treatments were prepared as shown below:

| Treatment No. | Container | Media (five [5] ml) |
|---|---|---|
| B1 | C1 | M4 |
| B2 | C2 | M4 |
| B3 | C3 | M4 |

Each sample was:
1) was incubated at room temperature for fort-eight (48) hours;
2) at approximate times after initial test of 1 hour, 3 hours, 6 hours, 9 hours, 24 hours, and 48 hours, the samples were gently mixed and after manual volume measurement of an aliquot, analyzed for: concentration, motility, rapid cells, VAP, VSL, VCL, ALH, BCF, STR, and LIN using a CASA with bovine specific software. (Version 12 software for IVOS) This process for each sample was terminated upon detection of no remaining motility. Additionally, slides were prepared at approximate times after initial test of 1 hour, 6 hours, and 24 hours for analysis of morphology, mitochondrial intactness, and DNA.
3) The resulting data were analyzed using ANOVA with mean comparison at analysis time point.

B. Acrosome Testing

Acrosome determinations were made using the chlortetracycline technique of chlortetracycline fluorescence assay (Lee et al., 1987) using the samples fixed in glutaraldehyde.

A saturated solution of chlortetracycline stain was prepared just prior to use by filling a 50 mL conical centrifuge tube to the 5 mL line with powdered chlortetracycline. Approximately 35 mL of water was then added to the tube and the contents mixed. Because this chemical is light sensitive, it is important that this procedure be accomplished with very faint lighting (just enough lighting that would allow the technician to properly follow the procedure). The mixture was then filtered using 22 μm, 100 ml Nalgen filter (Nalgen Nunc International; Rochester, N.Y.) and then poured into a fresh standard 50 mL conical tube that was labeled with the current date and a date one week from that time. The labeled tube with filtered mixture was wrapped in aluminum foil to prevent light from entering. At this point, the filtered chlortetracycline was ready for use by the technician. This process was repeated once weekly until all acrosome assays had been completed.

At each time point, the acrosome reaction was evaluated using a fluorescent microscope, equipped with a 520 μm excitation filter and a 570 μm barrier filter, the intact acrosome cap appears a fluorescent yellow. A total of 100 cells were evaluated per slide.

C. Leaching Analysis

A study was conducted to determine if antioxidants leached from test containers as follows:
1) 5 ml of media was placed in containers of types C1, C2, and C3.
2) At times 0 hours, 1 hour, 3 hours, 6 hours, 9 yours, and 24 hours, 0.5 ml of media was tested for the presence of the antioxidants.
3) At no time where the antioxidants found to present in the media in any of Type 1, Type 2, or Type 3 Containers.

D. Film Testing

Tests of film samples were performed on 6 films prepared as described above. The results were analyzed to compare the effect of a number of antioxidants. Film experiment were performed as follows:
1) Prior to semen sample collection, standard 24 well culture plates were outfitted with 6 sq. mm of their assigned plastic film.
2) Three semen samples between 1-4 hours old were obtained from the clinical lab following routine semen analysis.
3) At the start, the deidentified samples were vortexed for 10-15 seconds and underwent a second semen analysis using a Hamilton thorn IVOS-computer-assisted semen analyzer, collecting all available parameters.
4) Samples were washed using Fujifilm/Irvine multipurpose handling media ("MHM") by adding two ml of MHM to the tube, vortexing 10-15 seconds to mix, and centrifuging at 600 rpm for 6 minutes.
5) The supernatant was discarded, and 6.5 ml of fresh MHM was added to each sample, and the samples were vortexed to mix.
6) 0.5 ml of the sperm sample was placed in each experimental well, and the plate was cultured at room temperature for 24 hours.
7) Semen analysis was repeated at times 1 hour, 3 hours, 12 hours, and 24 hours.

VII. RESULTS

A. Human Results

Test result at a number of time intervals for collection and storage of prepared human semen samples in containers of types C1, C2 and C3 are reported in Tables 1 and 2, below.

TABLE 1

| | Test Results Test time* (hours) | | | | | | | | | | | |
|---|---|---|---|---|---|---|---|---|---|---|---|---|
| | 0 | | | 1 | | | 3 | | | 6 | | |
| | Container type | | | | | | | | | | | |
| Test Parameter | C1 | C2 | C3 | C1 | C2 | C3 | C1 | C2 | C3 | C1 | C2 | C3 |
| Concentration (M/ml) | 82.6 | 72.1 | 76.0 | 74.4 | 77.2 | 83.2 | 75.6 | 74.4 | 79.3 | 67.9 | 67.6 | 76.5 |
| Motility (normalized**, %) | 97.5 | 94.1 | 93.0 | 92.1 | 115.1 | 91.3 | 89.8 | 92.9 | 83.7 | 55.6 | 69.7 | 70.0 |
| Rapid Cells (normalized**,%) | 96.4 | 95.2 | 99.7 | 84.1 | 113.8 | 92.0 | 83.2 | 91.2 | 88.4 | 47.7 | 64.5 | 70.4 |
| VAP (μm/sec) | 57.6 | 56.1 | 57.9 | 53.8 | 58.2 | 56.0 | 53.3 | 55.4 | 57.5 | 43.9 | 44.7 | 47.8 |
| VSL (μm/sec) | 48.1 | 47.4 | 47.8 | 44.9 | 48.4 | 46.4 | 44.8 | 46.2 | 47.3 | 35.3 | 36.2 | 39.0 |
| VCL (μm/sec) | 93.7 | 88.6 | 94.6 | 85.9 | 91.2 | 91.4 | 84.2 | 86.6 | 93.3 | 71.0 | 72.5 | 78.0 |
| Elongation (μm) | 66.4 | 66.0 | 65.8 | 66.3 | 65.1 | 65.1 | 65.6 | 66.1 | 65.6 | 65.7 | 65.8 | 65.3 |
| ALH (μm) | 4.65 | 4.32 | 4.50 | 4.26 | 4.02 | 4.28 | 4.17 | 3.98 | 4.33 | 3.86 | 3.83 | 4.17 |
| BCF (Hz) | 26.6 | 23.1 | 25.1 | 27.4 | 25.0 | 27.4 | 26.3 | 24.4 | 26.4 | 21.1 | 23.6 | 24.1 |
| STR (%) | 81.6 | 82.2 | 80.9 | 81.9 | 82.3 | 80.6 | 82.3 | 81.8 | 80.1 | 79.0 | 79.7 | 79.6 |
| LIN (%) | 51.4 | 53.6 | 51.1 | 51.8 | 53.8 | 51.0 | 52.9 | 53.6 | 50.7 | 49.7 | 50.1 | 49.9 |

*Time measured from start time of test
**Normalized against the preprocessed sample time 0 is immediately after processing Since these tests were performed incubating the prepared semen samples at 37° C., degradation of the sperm is accelerated to simulate a longer test period during normal use of these containers at room temperature, such that 6 hours in these tests is believed to approximate 24 hours during normal use. Table 1 shows comparable values for container C1, C2, and C3 at the start of the experiment. Although samples were collected from 10 donors, data is reported for 9 donors since results for the rejected donor were outside statistical norms in terms of the sperm samples from this donor showing unusual resiliency regardless of storage conditions.

The three container types remain competitive at 1 hour. At 3 hours, semen samples in C3 containers show better results than for C1 and C2 containers for VAP, VSL, VCL, ALH, and BCF, while remaining comparable for motility, rapid cells, elongation, STR, and LIN. At 6 hours, semen samples in C3 containers show better results than for C1 and C2 containers for motility, rapid cells, VAP, VSL, VCL, ALH, and BCF, while remaining comparable for elongation, STR, and LIN.

At 3 hours, semen samples in C3 containers show better results than for C1 and C2 containers for VAP, VSL, VCL, ALH, and BCF, with values for rapid cells, elongation, STR, and LIN for samples in C3 containers being 95% or more of the same parameters measured for samples in C2 containers. Therefore, at 3 hours C3 containers perform the best for 5 parameters and nearly equal to the second best performer, C2 containers, on 4 other parameters.

At 6 hours, semen samples in C3 containers show better results than for C1 and C2 containers for normalized motility, rapid cells, VAP, VSL, VCL, elongation, ALH, and BCF, with values for STR and LIN for samples in C3 containers being 99% or more of the same parameters measured for samples in C2 containers. Therefore, at 6 hours C3 containers perform the best for 8 parameters and nearly equal to the second best performer, C2 containers, on 2 other parameters.

TABLE 2

| | Test Results Test time* (hours) | | | | | | | | |
|---|---|---|---|---|---|---|---|---|---|
| | 9 | | | 12 | | | 24 | | |
| | Container type | | | | | | | | |
| Test Parameter | C1 | C2 | C3 | C1 | C2 | C3 | C1 | C2 | C3 |
| Concentration (M/ml) | 65.0 | 62.0 | 60.0 | 65.0 | 65.7 | 61.3 | 52.0 | 48.6 | 51.1 |
| Motility (normalized, %) | 36.7 | 39.6 | 29.2 | 16.6 | 31.2 | 12.0 | 11.6 | 4.6 | 12.5 |
| Rapid Cells (normalized, %) | 29.8 | 33.5 | 25.0 | 13.1 | 27.6 | 9.7 | 2.2 | 1.9 | 5.6 |
| VAP (μm/sec) | 36.2 | 32.1 | 36.9 | 27.0 | 24.3 | 20.5 | 6.2 | 9.8 | 6.2 |
| VSL (μm/sec) | 28.0 | 25.3 | 28.4 | 21.4 | 19.0 | 16.0 | 5.5 | 6.8 | 5.1 |
| VCL (μm/sec) | 59.1 | 52.2 | 60.5 | 43.8 | 40.5 | 34.3 | 15.5 | 18.9 | 11.2 |
| Elongation (μm) | 67.3 | 59.3 | 68.4 | 62.4 | 52.4 | 36.2 | 26.7 | 22.7 | 13.4 |
| ALH (μm) | 3.58 | 3.21 | 3.83 | 2.51 | 2.31 | 2.18 | 1.12 | 0.78 | 0.98 |
| BCF (Hz) | 20.4 | 22.6 | 23.3 | 14.8 | 21.9 | 13.6 | 8.8 | 7.9 | 6.7 |
| STR (%) | 75.9 | 68.6 | 75.2 | 61.7 | 57.0 | 42.1 | 29.8 | 23.3 | 16.6 |
| LIN (%) | 47.3 | 42.7 | 47.2 | 40.2 | 35.0 | 25.2 | 13.3 | 12.5 | 9.2 |

*Time measured from start time of test

In Table 2, results at 9 hours, semen samples in C3 containers show better results than for C1 and C2 containers for motility, rapid cells, VAP, VSL, VCL, elongation, and ALH, while remaining comparable for BCF, STR, and LIN.

Data for 12 hours and 24 hours in Table 2 is believed to be less accurate due to the accelerated aging at 37° C. Additionally, although average values are reported at 24 hours as there was a failure to record results for 3 donors. This is believed to be due to end-of-life conditions for the sperm.

These results are believed to show that C3 containers would show superior performance compared to C1 and C2 containers during the time period from 0 to 24 hours after collection when used at room temperature.

In sum, Tables 1 and 2 are believed to show a preference for the combination of antioxidants A3 and A4 over the combination of antioxidants A3 and A5.

B. Equine Results

Test result at a number of time intervals for collection and storage of prepared equine semen samples in containers of types C4, C5, and C6 are reported in Tables 3 and 4, below.

ity, rapid cells, BCF, and LIN, with values for VAP, VSL, VCL, elongation, and STR for samples in C6 containers being 97% or more of the same parameters measured for samples in C5 containers. Therefore, at 9 hours C6 containers perform the best for 4 parameters and nearly equal to the second best performer, C5 containers, on 5 other parameters.

At 12 hours, semen samples in C6 containers show better results than for C4 and C5 containers for normalized motility, elongation, BCF, and STR, with values for VAP, VSL, VCL, ALH, and LIN for samples in C6 containers being 96% or more of the same parameters measured for samples in C5 containers. Therefore, at 12 hours C6 containers perform the best for 4 parameters and nearly equal to the second best performer, C5, on 5 other parameters.

At 24 hours, semen samples in C6 containers show better results than for C4 and C5 containers for normalized motil-

TABLE 3

| | Test Results Test time* (hours) | | | | | | | | | | | |
|---|---|---|---|---|---|---|---|---|---|---|---|---|
| | 6 | | | 9 | | | 12 | | | 24 | | |
| | Container type | | | | | | | | | | | |
| Test Parameter | C4 | C5 | C6 | C4 | C5 | C6 | C4 | C5 | C6 | C4 | C5 | C6 |
| Concentration (M/ml) | 63.9 | 75.9 | 62.1 | 62.2 | 80.8 | 63.1 | 68.8 | 84.7 | 64.7 | 66.4 | 68.4 | 71.5 |
| Motility (normalized, %) | 89.5 | 101.7 | 95.8 | 97.3 | 99.3 | 105.0 | 100.5 | 100.8 | 105.0 | 38.9 | 32.7 | 50.8 |
| Rapid Cells (normalized, %) | 114.2 | 156.8 | 142.3 | 120.4 | 155.3 | 133.4 | 121.7 | 146.1 | 130.6 | 27.2 | 29.1 | 42.6 |
| VAP (µm/sec) | 102.9 | 120.0 | 116.6 | 110.8 | 117.1 | 113.4 | 110.7 | 112.6 | 111.3 | 54.6 | 57.3 | 66.7 |
| VSL (µm/sec) | 62.5 | 75.4 | 74.2 | 61.0 | 68.2 | 66.6 | 60.2 | 65.0 | 62.6 | 32.2 | 36.8 | 40.9 |
| VCL (µm/sec) | 194.0 | 223.5 | 213.4 | 217.5 | 225.3 | 223.3 | 217.1 | 216.4 | 216.3 | 116.6 | 113.2 | 133.9 |
| Elongation (µm) | 59.7 | 61.4 | 60.4 | 60.9 | 62.0 | 60.1 | 60.0 | 60.3 | 60.7 | 58.3 | 57.9 | 57.6 |
| ALH (µm) | 7.69 | 8.13 | 7.59 | 8.44 | 8.62 | 7.98 | 8.38 | 8.43 | 8.06 | 8.18 | 8.00 | 7.87 |
| BCF (Hz) | 32.6 | 30.9 | 35.4 | 30.2 | 29.8 | 33.2 | 30.9 | 29.5 | 32.6 | 26.9 | 26.7 | 27.8 |
| STR (%) | 61.3 | 61.8 | 63.2 | 55.8 | 58.0 | 57.9 | 54.6 | 57.1 | 57.4 | 60.4 | 61.9 | 60.3 |
| LIN (%) | 34.8 | 34.9 | 36.9 | 29.2 | 31.0 | 31.5 | 28.7 | 30.5 | 30.5 | 29.6 | 33.8 | 31.2 |

*Time measured from start time of test

The three container types all show sufficient performance at 6 hours, with container C6 results being the best for just BCF, STR, and LIN, with values for normalized motility, VAP, VSL, VCL, and elongation for samples in C6 containers being 94% or more of the same parameters measured for samples in the second best performer, C5 containers. Therefore, at 6 hours C6 containers perform the best for 3 parameters and nearly equal to the second best performer, C5 containers, on 5 other parameters.

At 9 hours, semen samples in C6 containers show better results than for C4 and C5 containers for normalized motility, rapid cell, VAP, VSL, VCL, and BCF, with values for elongation, ALH, and STR for samples in C6 containers being 97% or more of the same parameters measured for samples in C5 containers. Therefore, at 24 hours C6 containers perform the best for 6 parameters and nearly equal to the second best performer, C5, on 3 other parameters.

In aggregate, the data from 6 to 24 hours shows a trend toward container C6 showing an increasing performance advantage with time.

TABLE 4

| | Test Results Test time* (hours) | | | | | | | | |
|---|---|---|---|---|---|---|---|---|---|
| | 48 | | | 72 | | | 96 | | |
| | Container type | | | | | | | | |
| Test Parameter | C4 | C5 | C6 | C4 | C5 | C6 | C4 | C5 | C6 |
| Concentration (M/ml) | 68.1 | 69.0 | 71.5 | 66.2 | 60.5 | 65.9 | 51.8 | 56.8 | 60.6 |
| Motility (normalized, %) | 11.2 | 15.7 | 26.0 | 9.9 | 12.6 | 17.2 | 8.0 | 6.2 | 7.8 |
| Rapid Cells (normalized, %) | 7.2 | 8.4 | 15.6 | 4.3 | 9.0 | 13.4 | 3.6 | 5.6 | 4.2 |
| VAP (µm/sec) | 47.7 | 44.5 | 45.1 | 44.9 | 60.9 | 50.6 | 49.4 | 48.8 | 43.2 |
| VSL (µm/sec) | 27.6 | 27.6 | 29.8 | 29.6 | 44.6 | 31.2 | 33.9 | 30.2 | 28.7 |
| VCL (µm/sec) | 94.3 | 87.4 | 88.6 | 88.4 | 103.7 | 101.6 | 87.4 | 94.6 | 81.5 |
| Elongation (µm) | 54.9 | 57.0 | 51.6 | 54.2 | 60.3 | 55.6 | 56.7 | 61.4 | 51.9 |

TABLE 4-continued

| | Test Results Test time* (hours) | | | | | | | | |
|---|---|---|---|---|---|---|---|---|---|
| | 48 | | | 72 | | | 96 | | |
| | Container type | | | | | | | | |
| Test Parameter | C4 | C5 | C6 | C4 | C5 | C6 | C4 | C5 | C6 |
| ALH (μm) | 8.45 | 7.29 | 7.06 | 8.05 | 7.34 | 6.67 | 7.54 | 7.86 | 8.05 |
| BCF (Hz) | 22.2 | 25.2 | 21.8 | 30.4 | 20.8 | 28.1 | 27.1 | 25.7 | 21.3 |
| STR (%) | 57.9 | 58.2 | 56.0 | 60.5 | 67.0 | 59.4 | 63.7 | 58.6 | 57.0 |
| LIN (%) | 30.8 | 33.1 | 31.9 | 35.2 | 42.9 | 32.2 | 41.0 | 35.2 | 33.9 |

*Time measured from start time of test

At 48 hours, semen samples in C6 containers show better results than for C4 and C5 containers for normalized motility, rapid cells, VAP, VSL, and VCL, with values for ALH, STR, and LIN for samples in C6 containers being 96% or more of the same parameters measured for samples in C5 containers. Therefore, at 48 hours C6 containers perform the best for 5 parameters and nearly equal to the second best performer, C5 containers, on 4 other parameters.

At 72 hours, semen samples in C6 containers show better results than for C4 and C5 containers for normalized motility, rapid cells, and BCF, with values for VCL, elongation, and ALH for samples in C6 containers being 91% or more of the same parameters measured for samples in C5 containers. Therefore, at 72 hours C6 containers perform the best for 3 parameters and nearly equal to the second best performer, C5 containers, on 3 other parameters.

At 96 hours, semen samples in C6 containers show better results than for C4 and C5 containers for normalized motility and ALH, with values for VSL, STR, and LIN for samples in C6 containers being 95% or more of the same parameters measured for samples in C5 containers. Therefore, at 96 hours C6 containers perform the best for 2 parameters and nearly equal to the second best performer, C5 containers, on 3 other parameters.

In sum, Tables 3 and 4 are believed to show that C6 containers show equal or superior performance compared to C4 and C5 containers during the time period from 0 to 96 hours after start of testing.

These results are also believed to show a preference for the combination of antioxidants A3 and A4 over the combination of antioxidants A3 and A5.

C. Bovine Results

Test result at a number of time intervals for collection and storage of prepared bovine semen samples in containers of types C1, C2 and C3 are reported in Tables 5 and 6, below. Acrosome analysis results are shown in Table 7.

TABLE 5

| | Test Results Test time* (hours) | | | | | | | | | | | |
|---|---|---|---|---|---|---|---|---|---|---|---|---|
| | 1 | | | 3 | | | 6 | | | 9 | | |
| | Container type | | | | | | | | | | | |
| Test Parameter | C1 | C2 | C3 | C1 | C2 | C3 | C1 | C2 | C3 | C1 | C2 | C3 |
| Concentration (M/ml) | 25.0 | 25.6 | 21.0 | 30.6 | 22.7 | 16.8 | 41.0 | 32.6 | 27.3 | 37.1 | 35.9 | 25.5 |
| Motility (normalized, %) | 57.9 | 65.1 | 85.4 | 36.3 | 60.1 | 74.4 | 27.2 | 36.2 | 72.5 | 11.1 | 32.7 | 29.7 |
| Rapid Cells (normalized, %) | 48.5 | 66.6 | 68.5 | 29.7 | 48.7 | 50.8 | 19.7 | 31.7 | 52.4 | 5.3 | 29.9 | 32.1 |
| VAP (μm/sec) | 73.8 | 88.8 | 74.9 | 73.8 | 74.7 | 70.7 | 54.5 | 86.1 | 67.2 | 57.5 | 87.0 | 84.5 |
| VSL (μm/sec) | 54.7 | 70.6 | 53.8 | 54.4 | 55.2 | 54.2 | 37.6 | 71.8 | 50.2 | 38.7 | 64.2 | 68.9 |
| VCL (μm/sec) | 155.9 | 177.7 | 153.4 | 147.4 | 151.3 | 143.3 | 124.2 | 160.2 | 138.7 | 107.2 | 170.4 | 169.1 |
| Elongation (μm) | 41.7 | 42.7 | 39.3 | 37.3 | 45.0 | 47.3 | 40.3 | 37.7 | 41.7 | 50.0 | 40.0 | 43.3 |
| ALH (μm) | 7.27 | 8.43 | 8.03 | 8.13 | 8.37 | 7.70 | 6.17 | 7.73 | 7.87 | 2.67 | 6.17 | 7.07 |
| BCF (Hz) | 28.4 | 27.7 | 27.2 | 25.7 | 28.1 | 27.6 | 17.8 | 35.5 | 32.4 | 21.0 | 33.9 | 32.4 |
| STR (%) | 69.0 | 77.3 | 69.0 | 74.3 | 74.7 | 76.3 | 66.7 | 81.0 | 78.7 | 70.0 | 75.7 | 80.7 |
| LIN (%) | 36.7 | 40.7 | 36.3 | 38.7 | 38.0 | 39.3 | 31.0 | 45.3 | 45.0 | 38.7 | 40.7 | 43.0 |

* Time measured from start time of test

Table 5 shows normalized motility of cryopreserved bovine semen samples incubated at standard room temperature (21° C.-23° C.) in a containers C1, C2, and C3 trends substantially higher for container C3 than for containers C1 and C2 for at least the first 6 hrs post-thaw (P<0.006), while remaining competitive at 9 hours.

Table 5 further shows normalized motility of cryopreserved bovine semen samples incubated at standard room temperature (21° C.-23° C.) in a containers C1, C2, and C3 trends substantially higher for container C3 than for containers C1 and C2 for all times tested through the first 9 hours.

The three container types remain competitive at 1 hour. At 3 hours, semen samples in C3 containers show better results than for C1 and C2 containers for VAP, VSL, VCL, ALH, and BCF, while remaining comparable for motility, rapid cells, elongation, STR, and LIN. At 6 hours, semen samples in C3 containers show better results than for C1 and C2 containers for motility, rapid cells, VAP, VSL, VCL, ALH, and BCF, while remaining comparable for elongation, STR, and LIN.

At 3 hours, semen samples in C3 containers show better results than for C1 and C2 containers for normalized motility, rapid cell, elongation, STR, and LIN, with values for VAP, VSL, VCL, and BCF for samples in C3 containers being 95% or more of the same parameter measured for samples in C2 containers. Therefore, at 3 hours C3 containers perform the best for 5 parameters and substantially equal to the second best performer, C2 containers, on 4 other parameters.

At 6 hours, semen samples in C3 containers show better results than for C1 and C2 containers for normalized motility, rapid cell, elongation, and ALH, with values for STR and LIN for samples in C3 containers being 97% or more of the same parameter measured for samples in C2 containers. Therefore, at 6 hours C3 containers perform the best for 4 parameters and substantially equal to the second best performer, C2 containers, on 2 other parameters.

At 9 hours, semen samples in C3 containers show better results than for C1 and C2 containers for rapid cell, VSL, elongation, ALH, STR, and LIN, with values for VAP, VSL, and BCF for samples in C3 containers being 96% or more of the same parameter measured for samples in C2 containers. Therefore, at 9 hours C3 containers perform the best for 6 parameters and substantially equal to the second best performer, C2 containers, on 3 other parameters.

TABLE 6

| | Test Results Test time* (hours) | | | | | |
|---|---|---|---|---|---|---|
| | 24 | | | 48 | | |
| | Container type | | | | | |
| Test Parameter | 1 | 2 | 3 | 1 | 2 | 3 |
| Concentration (M/ml) | 48.1 | 35.1 | 33.7 | 42.4 | 36.0 | 23.9 |
| Motility (normalized, %) | 6.9 | 28.9 | 34.4 | 6.9 | 24.5 | 22.0 |
| Rapid Cells (normalized, %) | 1.8 | 28.7 | 29.3 | 2.6 | 22.3 | 17.1 |
| VAP (μm/sec) | 26.9 | 72.9 | 60.2 | 14.4 | 48.0 | 42.6 |
| VSL (μm/sec) | 18.7 | 58.9 | 48.4 | 11.0 | 34.9 | 36.1 |
| VCL (μm/sec) | 50.7 | 165.2 | 119.5 | 28.4 | 93.9 | 86.6 |
| Elongation (μm) | 29.0 | 42.3 | 43.3 | 13.3 | 28.0 | 30.3 |
| ALH (μm) | 2.20 | 6.67 | 6.77 | 2.10 | 4.30 | 3.13 |
| BCF (Hz) | 18.9 | 31.4 | 25.4 | 7.0 | 14.5 | 25.8 |
| STR (%) | 45.7 | 75.7 | 75.7 | 26.3 | 47.7 | 56.0 |
| LIN (%) | 25.3 | 34.3 | 42.0 | 9.3 | 26.0 | 29.3 |

*Time measured from start time of test

Table 6 shows normalized motility of cryopreserved bovine semen samples incubated at standard room temperature (21° C.-23° C.) in a containers C1, C2, and C3 continues the trend of container C3 outperforming containers C1 and C2 at 24 hours, while remaining competitive at 48 hours.

At 24 hours, semen samples in C3 containers show better results than for C1 and C2 containers for normalized motility, rapid cells, elongation, ALH, and LIN, with values for STR for samples in C3 containers being equal to the same parameter measured for samples in C2 containers. Therefore, at 9 hours C3 containers perform the best for 5 parameters and equal to the second best performer, C2 containers, on 1 other parameter.

At 48 hours, semen samples in C3 containers show better results than for C1 and C2 containers for VSL, elongation, BCF, STR, and LIN, with values for normalized motility and VCL for samples in C3 containers being 90% or more of the same parameter measured for samples in C2 containers. Therefore, at 48 hours C3 containers perform the best for 6 parameters and competitive with the second best performer, C2 containers, on 2 other parameter.

These results are also believed to show a preference for the combination of antioxidants A3 and A4 over the combination of antioxidants A3 and A5.

These results are believed to show that C3 containers would show superior performance compared to C1 and C2 containers during the time period from 0 to 24 hours after collection when used at room temperature.

In sum, Tables 5 and 6 are believed to show a preference for the combination of antioxidants A3 and A4 over the combination of antioxidants A3 and A5.

Acrosome Results (% cells intact)

TABLE 7

| Time | Container | | |
|---|---|---|---|
| (hrs)* | C1 | C2 | C3 |
| 1 | 30 | 42 | 41 |
| 6 | 11 | 37 | 40 |
| 24 | 4 | 29 | 36 |

*time from start of test

Acrosome status of cryopreserved bovine semen samples at 1, 6, and 24 hours post-thaw after incubation in a containers C1, C2, and C3. Cells incubated in the container C3 demonstrated significantly more intact acrosomes and functional mitochondria than container C1 at all times tested and container C2 at all times tested after 1 hour. Further, container C3 maintained significantly higher numbers of intact acrosomes thru 24 hours and more functional mitochondria from 6 hours when compared to container C2.

In summary, the human, equine, and bovine semen testing in containers C1, C2, and C3 show that container C3 has a new and useful combination of performance characteristics relative to containers C1 and C2. Although not every sperm attribute showed improvement with container C3 for every time tested, there were a significant number of attributes improved for a significant number of times tested indicating that sperm kinematics and morphology are maintained for a longer time period regardless of whether sperm was fresh, thawed, or incubated at higher temperature. In addition, results indicate P2 containing A3/A4 outperformed P1 containing A3/A5, or A4 resulting in better performance that A5.

D. Leaching Analysis

As mentioned above, no antioxidant compounds were detected in the media, suggesting all scavenging took place at the media/container interface as designed. At no time where the antioxidants found to present in the media in any of containers C1, C2, or C3.

E. Film Testing Results

TABLE 8

| | Test Results Test time* (hours) | | | | | | | | | | | |
|---|---|---|---|---|---|---|---|---|---|---|---|---|
| | 1 | | | | | | 3 | | | | | |
| | Film | | | | | | | | | | | |
| Test Parameter | F1 | F2 | F3 | F4 | F5 | F6 | F1 | F2 | F3 | F4 | F5 | F6 |
| Concentration (M/ml) | 16.9 | 18.0 | 35.0 | 14.3 | 16.8 | 22.4 | 11.3 | 26.3 | 20.0 | 18.4 | 18.5 | 12.0 |
| Motility (normalized, %) | 97 | 98 | 107 | 90 | 90 | 103 | 111 | 108 | 122 | 83 | 121 | 86 |
| Rapid Cells (normalized, %) | 103 | 100 | 112 | 74 | 100 | 112 | 121 | 96 | 101 | 90 | 125 | 98 |
| VAP (μm/sec) | 43.5 | 44.1 | 45.4 | 41.2 | 51.9 | 47.4 | 42.9 | 42.3 | 42.6 | 43.5 | 47.1 | 44.3 |
| VSL (μm/sec) | 30.6 | 33.0 | 34.3 | 31.7 | 40.1 | 38.3 | 31.7 | 31.6 | 32.4 | 33.2 | 35.5 | 31.9 |
| VCL (μm/sec) | 75.9 | 79.2 | 81.6 | 77.6 | 95.7 | 84.1 | 77.8 | 77.7 | 74.3 | 77.8 | 85.8 | 80.7 |
| Elongation (μm) | 67.0 | 65.7 | 66.7 | 66.3 | 63.0 | 64.0 | 65.0 | 67.0 | 68.0 | 68.3 | 67.0 | 67.3 |
| ALH (μm) | 5.0 | 4.9 | 4.8 | 5.2 | 5.3 | 4.9 | 5.5 | 5.7 | 4.9 | 4.7 | 4.9 | 5.2 |
| BCF (Hz) | 18.7 | 20.6 | 21.7 | 24.0 | 20.8 | 20.8 | 17.9 | 22.5 | 22.6 | 18.2 | 19.3 | 21.9 |
| STR (%) | 69.0 | 74.0 | 74.3 | 76.7 | 75.7 | 78.3 | 72.7 | 74.7 | 76.0 | 75.0 | 73.7 | 70.7 |
| LIN (%) | 40.3 | 42.7 | 42.7 | 42.0 | 44.0 | 45.3 | 41.3 | 41.7 | 44.0 | 43.0 | 41.7 | 40.0 |

*Time measured from start time of test

TABLE 9

| | Test Results Test time* (hours) | | | | | | | | | | | |
|---|---|---|---|---|---|---|---|---|---|---|---|---|
| | 12 | | | | | | 24 | | | | | |
| | Container type | | | | | | | | | | | |
| Test Parameter | F1 | F2 | F3 | F4 | F5 | F6 | F1 | F2 | F3 | F4 | F5 | F6 |
| Concentration (M/ml) | 10.7 | 27.5 | 15.7 | 15.6 | 7.5 | 19.9 | 11.1 | 23.5 | 15.9 | 11.3 | 8.3 | 12.9 |
| Motility (normalized, %) | 40 | 62 | 109 | 83 | 66 | 75 | 40 | 69 | 86 | 84 | 84 | 98 |
| Rapid Cells (normalized, %) | 38 | 60 | 107 | 79 | 65 | 80 | 41 | 67 | 83 | 90 | 95 | 103 |
| VAP (μm/sec) | 29.7 | 38.8 | 40.1 | 37.1 | 36.3 | 41.7 | 36.0 | 34.1 | 39.0 | 39.1 | 33.3 | 43.2 |
| VSL (μm/sec) | 19.6 | 28.0 | 28.7 | 25.8 | 24.8 | 29.3 | 23.7 | 24.7 | 27.5 | 27.6 | 23.5 | 31.8 |
| VCL (μm/sec) | 54.5 | 66.5 | 71.9 | 66.2 | 66.8 | 74.6 | 64.4 | 63.6 | 70.2 | 68.2 | 60.9 | 77.0 |
| Elongation (μm) | 42.7 | 65.0 | 65.3 | 68.0 | 72.7 | 70.0 | 70.0 | 72.0 | 67.0 | 71.7 | 67.3 | 70.0 |
| ALH (μm) | 4.0 | 3.9 | 5.1 | 3.7 | 3.7 | 4.6 | 4.1 | 5.3 | 3.7 | 3.0 | 4.0 | 4.6 |
| BCF (Hz) | 13.2 | 19.2 | 18.8 | 21.2 | 19.1 | 19.9 | 18.5 | 22.6 | 20.6 | 19.1 | 23.2 | 18.0 |
| STR (%) | 44.7 | 71.7 | 71.0 | 68.3 | 66.3 | 67.7 | 65.3 | 72.3 | 71.0 | 69.0 | 70.3 | 71.0 |
| LIN (%) | 24.7 | 42.7 | 40.0 | 39.3 | 37.3 | 38.0 | 38.7 | 41.7 | 39.7 | 40.3 | 38.3 | 40.3 |

*Time measured from start time of test

Normalized rapid cells values were evaluated as a good indicator of sample health and is simply the normalized value normalized rapid cells (observed rapid cells at time point/initial preprocessed observed*100 yielding %).

The overall measurement was a ranked sum of five values: normalized motility, normalized rapid cells, VAP, STR, and LIN. The six films were ranked best to worse for each single parameter (1-6) the resulting five sets of ranks were compared using ANOVA and Tukey's mean separation to establish differences in the reaction of the sperm cells to the films.

TABLE 10

| Film | Antioxidant | Mean % or Normalized Rapid Cells | Overall Comparison of Films |
|---|---|---|---|
| F1 | N/A | 90.1 | 2 |
| F2 | A1 | 94.1 | 5.8 |
| F3 | A2 | 106 | 6.4 |
| F4 | A3 | 95.7 | 5.6 |
| F5 | A4 | 81.1 | 2.6 |
| F6 | A6 | 108.1 | 6.6 |

Films F2, F3, F4, and F6 show improvement in mean % normalized rapid cells compared to the control film F1 without antioxidant. Film 5 underperforms compared to control film F1. Films F3 and F6 show the best performance. Films F2 and F4 show the second tier of performance behind F3 and F6.

Films F2, F3, F4, F5, and F6, all including antioxidant, show improvement overall comparison parameter. Films F3 and F6 show the best performance. Films F2 and F4 show the second tier of performance behind F3 and F6. Film F5 shows the third tier of performance behind F3 and F6.

Films F3 and F6 contain antioxidants A2 and A6 respectively. Films F2 and F4 contain antioxidants A1 and A3, respectively. Film F5 contains antioxidant A4. Results suggest hindered amine antioxidants provide better results than phosphite type antioxidants, and phosphite type antioxidants provide better results than phenol type antioxidants.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the apparatuses, methods, compositions, and/or devices described in the specification. As one of ordinary skill in the art will readily appreciate from the disclosure of the present invention, apparatuses, methods, compositions, and/or devices, presently existing or later to be developed that perform substantially the same function or achieve substantially the same result as the corresponding embodiments described herein, may be utilized according to the present invention. Accordingly, the appended claims are intended to include within their scope such apparatuses, methods, compositions, and/or devices.

What is claimed is:

1. An apparatus for collecting and/or storing biological fluid, the apparatus comprising:
    a first vessel having a collection means at the upper end of the first vessel and a reservoir at the lower end of the first vessel; and
    a second vessel, wherein:
    the first vessel is inserted into the second vessel, the first vessel has a first upper edge, the second vessel has a second upper edge; and the first upper edge and the second upper edge are substantially congruent;
    the collection means is configured to facilitate flow by gravity of the biological fluid into the reservoir;
    the first vessel comprises a blend of a polymer and an antioxidant;
    the reservoir has a first inner surface, and at least a portion of the first inner surface comprises the antioxidant in an amount effective to reduce oxidation damage to the biological fluid; and
    the antioxidant is selected from one or more of the group consisting of:
      a. a phenolic having a melting point greater than or equal to 60° C.;
      b. an aromatic amine;
      c. a sterically hindered amine;
      d. a hydroxylamine;
      e. an amine oxide derivative; and
      f. less than or equal to 0.1 wt. % of a phosphite and/or phosphonite, based on the weight of the blend.

2. The apparatus of claim 1, further comprising a lid suited for sealable attachment to the first vessel.

3. The apparatus of claim 2, further comprising a reservoir seal installed between the first vessel and the lid, wherein:
    the reservoir seal has a bottom surface surrounded by a seating surface at its lower end and a flange at its upper end, and
    full closure of the lid causes the flange to flex and provide force to engage the seating surface with the first vessel proximate a junction between the reservoir and the collection means such that the first inner surface of the reservoir and the bottom surface of the reservoir seal to define an enclosed chamber.

4. The apparatus of claim 1, wherein the first inner surface defines a volume within the reservoir and comprises geometric surface features suited to increase the ratio of the area of the first inner surface to the volume defined by the first inner surface.

5. The apparatus of claim 1, wherein the polymer comprises a thermoplastic.

6. The apparatus of claim 1, wherein the polymer is selected from one of the group of: acrylonitrile butadiene styrene, polyamide, polybutylene terephthalate, polycaprolactam, polycarbonate, polyether ether ketone, polyetherimide, polyethylene, polyethylene terephthalate, polymethyl methacrylate, polyoxymethylene, polyphenylene sulfide, polyphenylsulfone, polypropylene, polystyrene, polyvinylidene fluoride, styrene acrylonitrile resin, thermoplastic elastomers, thermoplastic polyurethane, or combinations thereof.

7. The apparatus of claim 1, wherein the antioxidant is chemically and/or physically bonded to the first inner surface.

8. An apparatus for collecting and/or storing biological fluid, the apparatus comprising:
    a first vessel having a collection means at the upper end of the first vessel and a reservoir at the lower end of the first vessel; and
    a second vessel, wherein:
    the first vessel is inserted into the second vessel, the first vessel has a first upper edge, the second vessel has a second upper edge; and the first upper edge and the second upper edge are substantially congruent;
    the collection means is configured to facilitate flow by gravity of the biological fluid into the reservoir;
    the first vessel comprises a blend of a polymer and less than or equal to 0.1 wt. % of an antioxidant based on the weight of the blend;
    the reservoir has a first inner surface, and at least a portion of the first inner surface comprises the antioxidant in an amount effective to reduce oxidation damage to the biological fluid; and
    the antioxidant is selected from one or more of the group consisting of:
      a. a phenolic having a melting point greater than or equal to 60° C.;
      b. an aromatic amine;
      c. a sterically hindered amine;
      d. a hydroxylamine;
      e. an amine oxide derivative; and
      f. a phosphite and/or phosphonite.

9. The apparatus of claim 8, further comprising a lid suited for sealable attachment to the first vessel.

10. The apparatus of claim 9, further comprising a reservoir seal installed between the first vessel and the lid, wherein:
    the reservoir seal has a bottom surface surrounded by a seating surface at its lower end and a flange at its upper end, and
    full closure of the lid causes the flange to flex and provide force to engage the seating surface with the first vessel proximate a junction between the reservoir and the collection means such that the first inner surface of the reservoir and the bottom surface of the reservoir seal to define an enclosed chamber.

11. The apparatus of claim 8, wherein the first inner surface defines a volume within the reservoir and comprises geometric surface features suited to increase the ratio of the area of the first inner surface to the volume defined by the first inner surface.

12. The apparatus of claim 8, wherein the polymer is selected from the group consisting of: acrylonitrile butadiene styrene, polyamide, polybutylene terephthalate, polycaprolactam, polycarbonate, polyether ether ketone, polyetherimide, polyethylene, polyethylene terephtalate, polymethyl methacrylate, polyoxymethylene, polyphenylene sulfide, polyphenylsulfone, polypropylene, polystyrene, polyvinylidene fluoride, styrene acrylonitrile resin, thermoplastic elastomers, thermoplastic polyurethane, or combinations thereof.

13. The apparatus of claim 8, wherein the antioxidant is chemically and/or physically bonded to the first inner surface.

14. An apparatus for collecting and/or storing biological fluid, the apparatus comprising:
a first vessel having a collection means at the upper end of the first vessel and a reservoir at the lower end of the first vessel; and
a second vessel, wherein:
the first vessel is inserted into the second vessel, the first vessel has a first upper edge, the second vessel has a second upper edge; and the first upper edge and the second upper edge are substantially congruent;
the collection means is configured to facilitate flow by gravity of the biological fluid into the reservoir;
the reservoir has a first inner surface;
the first inner surface comprises an antioxidant in an amount effective to reduce oxidation damage to the biological fluid; and
the antioxidant is selected from one or more of the group consisting of:
a. a phenolic having a melting point greater than or equal to 60° C.;
b. an aromatic amine;
c. a sterically hindered amine;
d. a hydroxylamine; and
e. an amine oxide derivative.

15. The apparatus of claim 14, further comprising a lid suited for sealable attachment to the first vessel.

16. The apparatus of claim 15, further comprising a reservoir seal installed between the first vessel and the lid, wherein:
the reservoir seal comprises a cylindrical body having a bottom surface surrounded by a seating surface at its lower end and a flexible flange at its upper end, and
full closure of the lid causes the flange to flex and provide force to engage the seating surface with the first vessel proximate a junction between the reservoir and the collection means such that the first inner surface of the reservoir and the bottom surface of the reservoir seal to define an enclosed chamber.

17. The apparatus of claim 14, wherein the first inner surface defines a volume within the reservoir and comprises geometric surface features suited to increase the ratio of the surface area of the first inner surface to the volume defined by the first inner surface.

18. The apparatus claim 14, wherein the first vessel comprises a polymer selected from the group consisting of: acrylonitrile butadiene styrene, polyamide, polybutylene terephthalate, polycaprolactam, polycarbonate, polyether ether ketone, polyetherimide, polyethylene, polyethylene terephthalate, polymethyl methacrylate, polyoxymethylene, polyphenylene sulfide, polyphenyl sulfone, polypropylene, polystyrene, polyvinylidene fluoride, styrene acrylonitrile resin, thermoplastic elastomers, thermoplastic polyurethane, or combinations thereof.

19. The apparatus of claim 14, wherein the antioxidant is chemically and/or physically bonded to the first inner surface.

20. The apparatus of claim 14, wherein a polymer comprising the antioxidant is bonded to the first inner surface.

21. An apparatus for collecting and/or storing biological fluid, the apparatus comprising:
a first vessel having a collection means at the upper end of the first vessel and a reservoir at the lower end of the first vessel; and
a second vessel, wherein:
the first vessel is inserted into the second vessel, the first vessel has a first upper edge, the second vessel has a second upper edge; and the first upper edge and the second upper edge are substantially congruent;
the collection means is configured to facilitate flow by gravity of the biological fluid into the reservoir;
the first vessel comprises a blend of a polymer and an antioxidant;
the reservoir has a first inner surface, and at least a portion of the first inner surface comprises the antioxidant in an amount effective to reduce oxidation damage to the biological fluid; and
the antioxidant is selected from one or more of the group consisting of:
a. an aromatic amine;
b. a sterically hindered amine;
c. a hydroxylamine; and
d. an amine oxide derivative.

22. The apparatus of claim 21, wherein the polymer composition further comprises a second antioxidant selected from one or more of the group consisting of:
a. a phenolic; and
b. a phosphite and/or phosphonite.

23. The apparatus of claim 21, further comprising a lid suited for sealable attachment to the first vessel.

24. The apparatus of claim 23, further comprising a reservoir seal installed between the first vessel and the lid, wherein:
the reservoir seal has a bottom surface surrounded by a seating surface at its lower end and a flange at its upper end, and
full closure of the lid causes the flange to flex and provide force to engage the seating surface with the first vessel proximate a junction between the reservoir and the collection means such that the first inner surface of the reservoir and the bottom surface of the reservoir seal to define an enclosed chamber.

25. The apparatus of claim 21, wherein the polymer is selected from the group of: acrylonitrile butadiene styrene, polyamide, polybutylene terephthalate, polycaprolactam, polycarbonate, polyether ether ketone, polyetherimide, polyethylene, polyethylene terephthalate, polymethyl methacrylate, polyoxymethylene, polyphenylene sulfide, polyphenylsulfone, polypropylene, polystyrene, polyvinylidene fluoride, styrene acrylonitrile resin, thermoplastic elastomers, thermoplastic polyurethane, or combinations thereof.

26. An apparatus for collecting and/or storing biological fluid, the apparatus comprising a first vessel having a collection means at the upper end of the first vessel and a reservoir at the lower end of the first vessel, wherein:

the collection means is configured to facilitate flow by gravity of the biological fluid into the reservoir;

the first vessel comprises a blend of a polymer and a first antioxidant;

the reservoir has a first inner surface, and at least a portion of the first inner surface comprises the antioxidant in an amount effective to reduce oxidation damage to the biological fluid; and wherein the first antioxidant is a sterically hindered amine.

27. The apparatus of claim 26, wherein the polymer composition further comprises a second antioxidant selected from one or more of the group consisting of:

a. a phenolic;
b. an aromatic amine;
c. a hydroxylamine;
d. an amine oxide derivative; and
e. a phosphite and/or phosphonite.

28. The apparatus of claim 27, wherein the second antioxidant is:

a. a phenolic; and/or
b. a phosphite and/or phosphonite.

* * * * *